US008017828B2

(12) United States Patent
Izumori et al.

(10) Patent No.: US 8,017,828 B2
(45) Date of Patent: Sep. 13, 2011

(54) UTILIZATION OF RARE SUGARS IN PLANT OR MICROORGANISM

(75) Inventors: Ken Izumori, Kagawa (JP); Kazuya Akimitsu, Kagawa (JP); Shigeyuki Tajima, Kagawa (JP); Mika Agarie, Kagawa (JP); Tomohiro Yanagi, Kagawa (JP); Ryosuke Mochioka, Sanuki (JP)

(73) Assignees: Shikoku Research Institute Incorporated, Takamatsu-shi (JP); National University Corporation Kagawa University, Takamatsu-shi (JP)

( * ) Notice: Subject to any disclaimer, the term of this patent is extended or adjusted under 35 U.S.C. 154(b) by 1095 days.

(21) Appl. No.: 11/569,576

(22) PCT Filed: May 24, 2005

(86) PCT No.: PCT/JP2005/009474
§ 371 (c)(1),
(2), (4) Date: Jul. 13, 2007

(87) PCT Pub. No.: WO2005/112638
PCT Pub. Date: Dec. 1, 2005

(65) Prior Publication Data
US 2008/0182752 A1    Jul. 31, 2008

(30) Foreign Application Priority Data

May 24, 2004 (JP) ................... 2004-153916
May 24, 2004 (JP) ................... 2004-153917
Sep. 24, 2004 (JP) ................... 2004-278372
Nov. 26, 2004 (JP) ................... 2004-342941

(51) Int. Cl.
*A01H 3/04*    (2006.01)
*C12N 15/01*   (2006.01)
*A01N 25/32*   (2006.01)
*A01N 43/08*   (2006.01)
*A01N 43/16*   (2006.01)
*C12P 19/02*   (2006.01)

(52) U.S. Cl. .............. 800/276; 435/105; 504/116.1; 504/140; 504/291; 504/292; 514/23

(58) Field of Classification Search .......... 800/276; 536/123.1, 124, 1.1; 435/105; 504/113
See application file for complete search history.

(56) References Cited

U.S. PATENT DOCUMENTS
5,340,404 A * 8/1994 McCulloch ............. 127/46.2
(Continued)

FOREIGN PATENT DOCUMENTS
JP    63-215606 A    9/1988
JP    10-36210 A     2/1998
JP    2004-300079 A  10/2004
(Continued)

OTHER PUBLICATIONS

Sato et al., "Effect of a rare sugar, D-psicose, on growth of an oligotrophic bacterium V-16," 1995, Kagawa Daigaku Nogakubu; 47(2): 127-132 (not supplied; inventors' publication).*

(Continued)

*Primary Examiner* — Johann Richter
*Assistant Examiner* — Jane C Oswecki
(74) *Attorney, Agent, or Firm* — Westerman, Hattori, Daniels & Adrian, LLP

(57) ABSTRACT

To provide an agricultural chemical and the like with the use of an effect of inducing systemic acquired resistance in a plant. To provide a growth inhibitor of not only a plant pathogenic bacterium but also a harmful microorganism. Utilization of a rare sugar for inducing systemic acquired resistance in a plant or inhibiting the growth of a microorganism. Utilization thereof as an agricultural chemical with the use of the effect of inducing systemic acquired resistance in a plant, a plant disease inhibitor, an inducer of a plant growth regulatory factor (i.e., an inducer of plant hormone-like actions consisting of disease resistance, insect resistance, fruit maturation, breaking of dormancy, regulation of germination, drying resistance, and other than this, resistance to environmental stresses such as low temperature resistance, high temperature resistance, salt resistance and heavy metal resistance and promotion of flowering) and a microorganism growth inhibitor. The rare sugar is an aldose (D-allose, D-altrose or L-galactose) or a ketose (D-psicose or a mixture of D-psicose and D-fructose).

11 Claims, 19 Drawing Sheets

U.S. PATENT DOCUMENTS 5,588,254 A 12/1996 Adachi et al.
2004/0023924 A1 2/2004 Lienart
2004/0198604 A1 10/2004 Umemura et al.

FOREIGN PATENT DOCUMENTS

WO    WO 03/020032 A1    3/2003

OTHER PUBLICATIONS

International Search Report of PCT/JP2005/009474, date of mailing: Jun. 28, 2005.

* cited by examiner

[Fig.1]
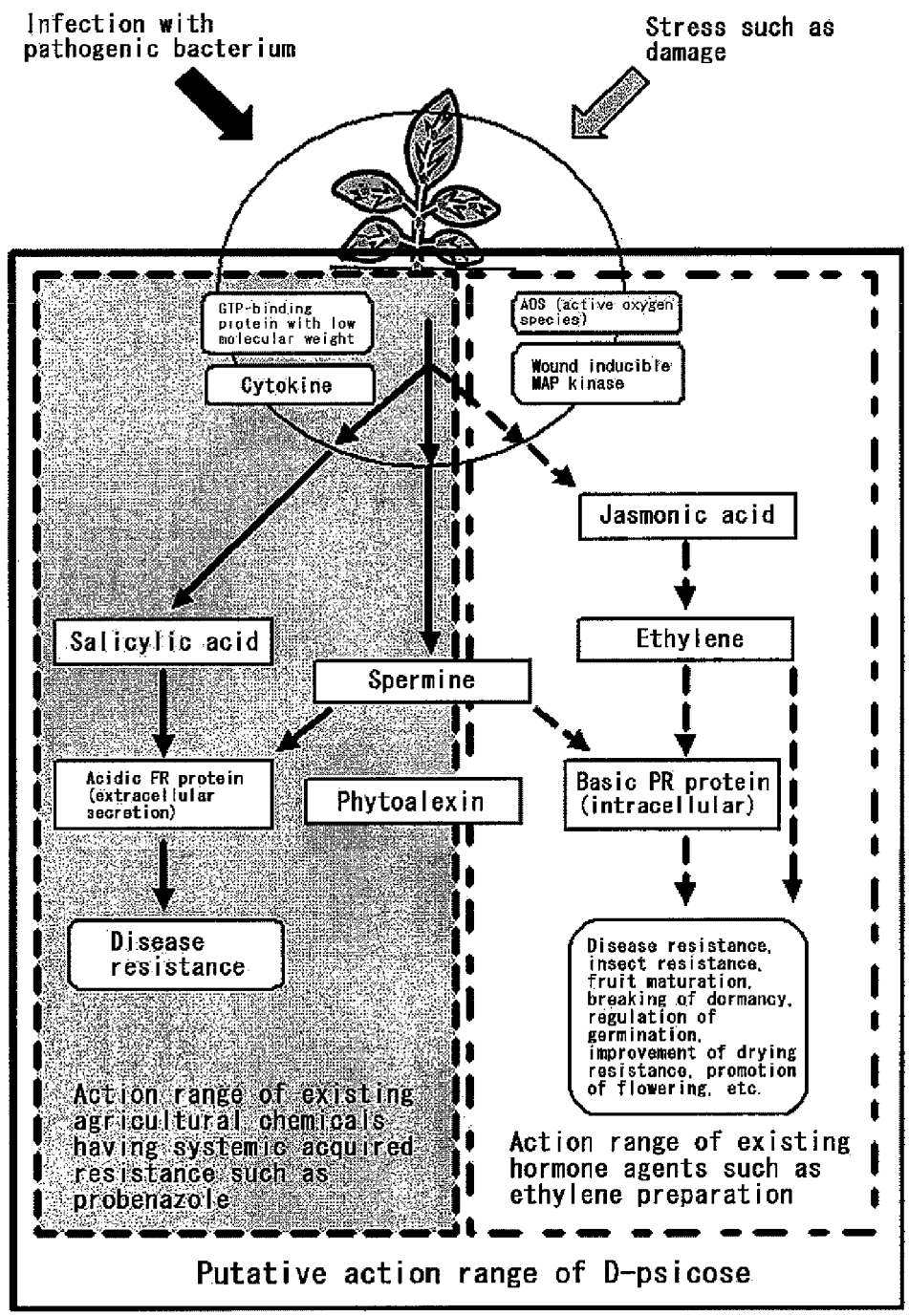

[Fig.2]
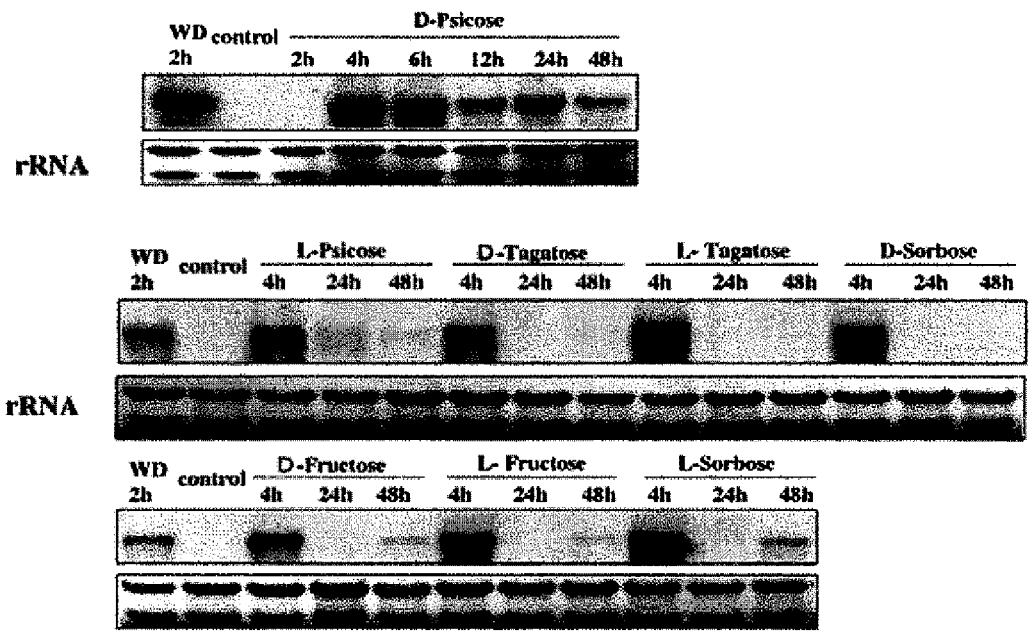
Northern analysis of LOX gene expression in rough lemon leaves. Total RNA was treated of rear sugars.
[Fig.3]
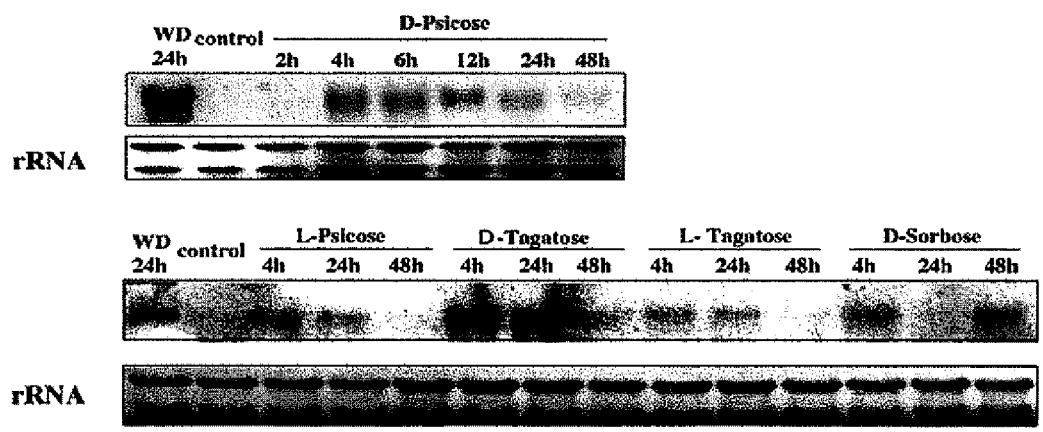
Northern analysis of Chi A gene expression in rough lemon leaves. Total RNA was treated of rear sugars.

[Fig.4]
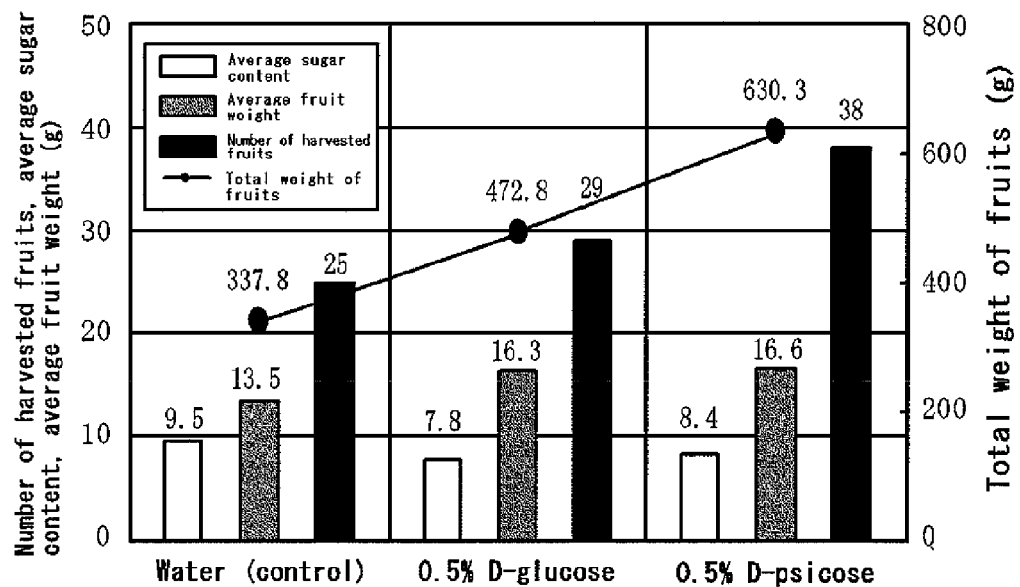
[Fig.5]
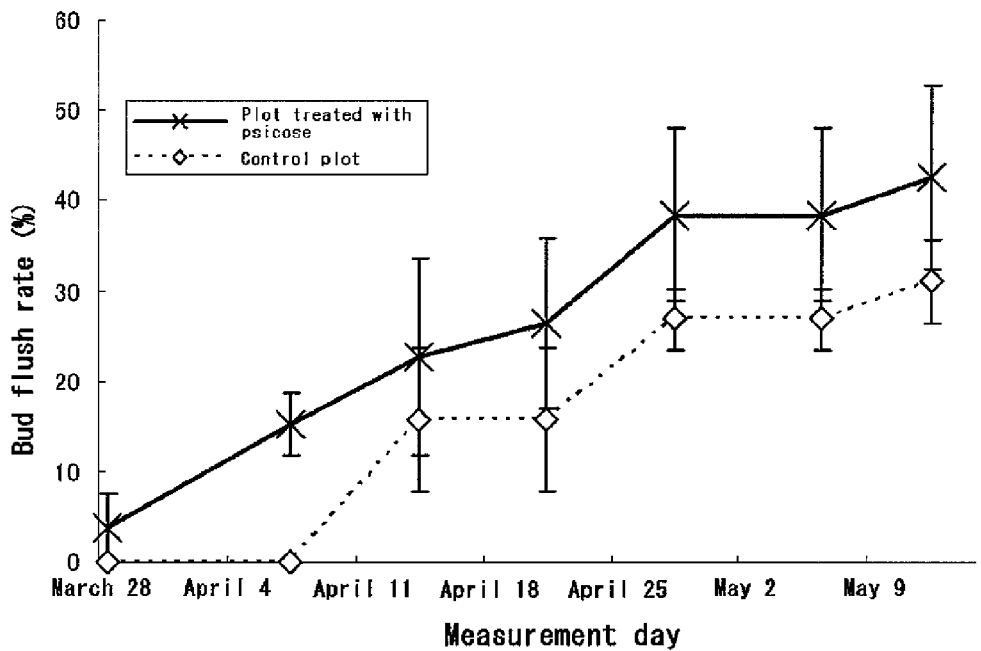

[Fig.6]
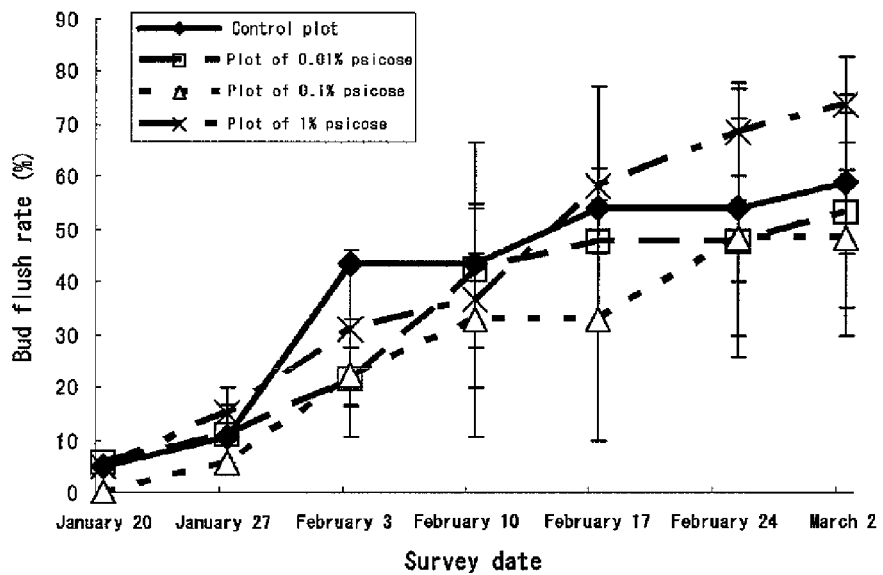
[Fig.7]
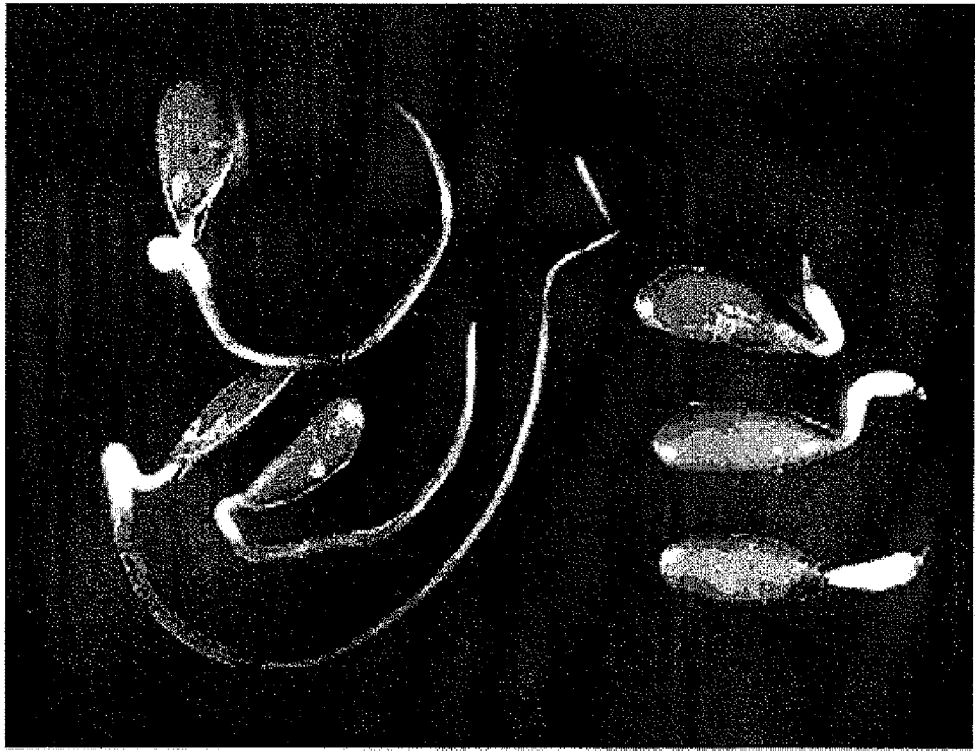

[Fig.8]
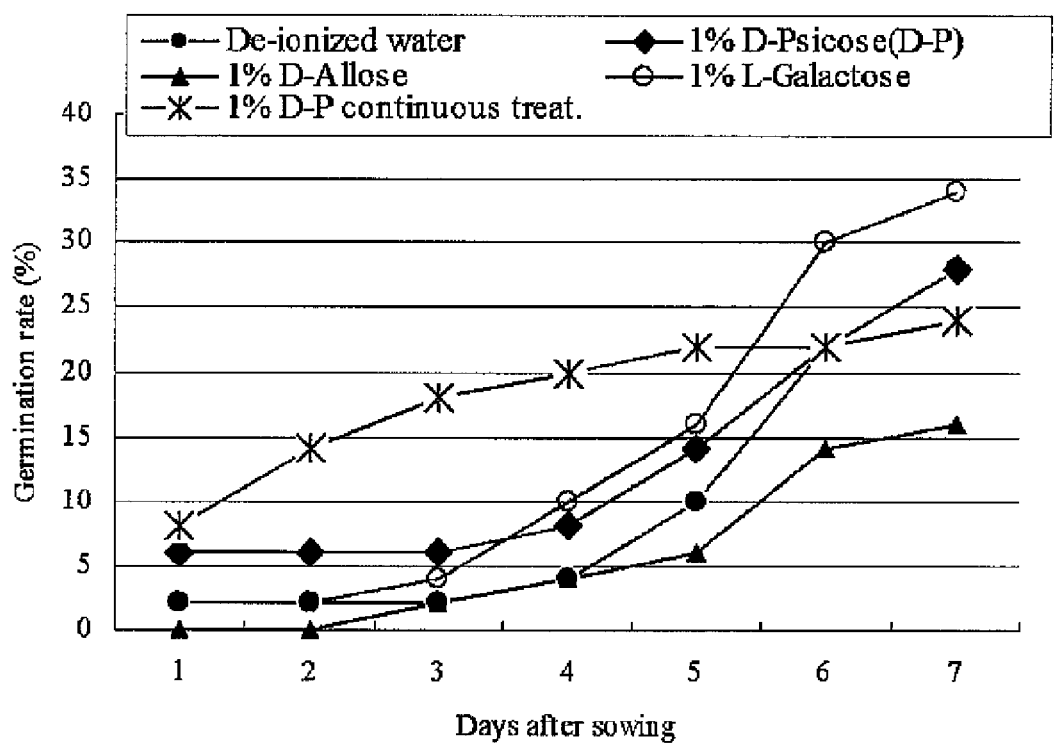

[Fig.9]
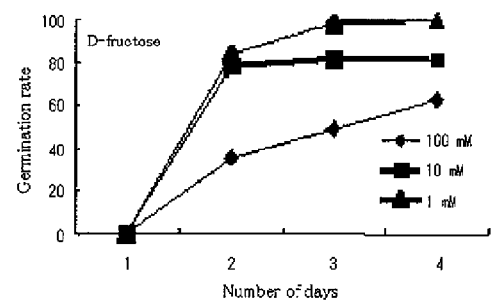
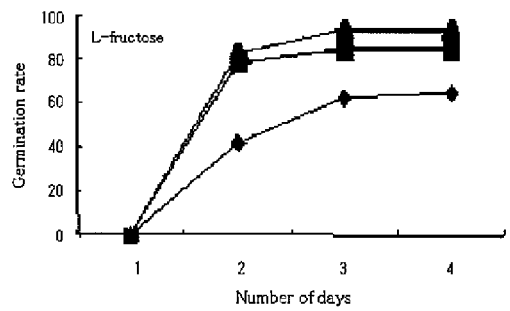
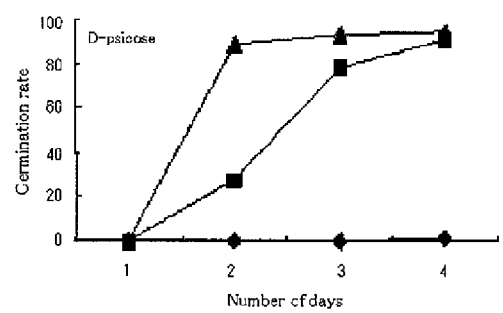
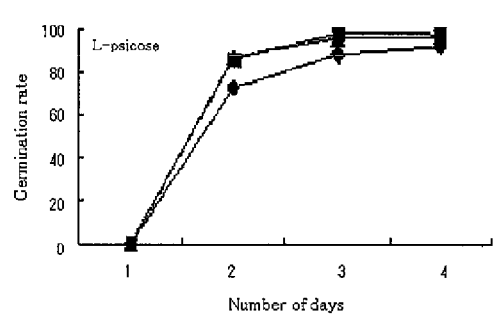
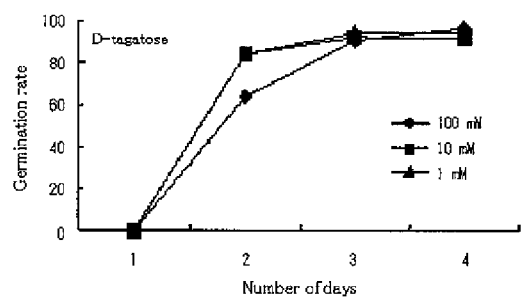
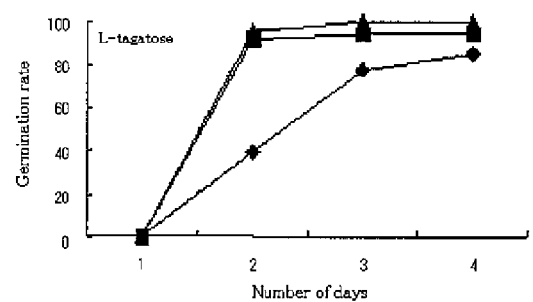
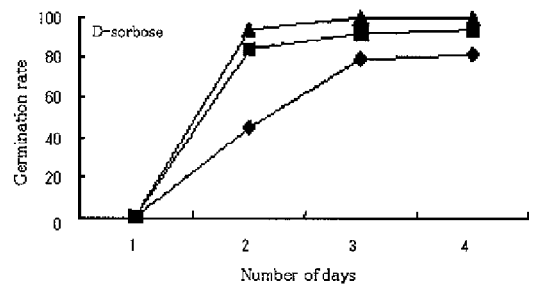
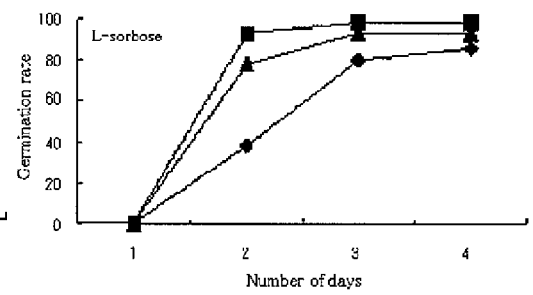

[Fig.10]
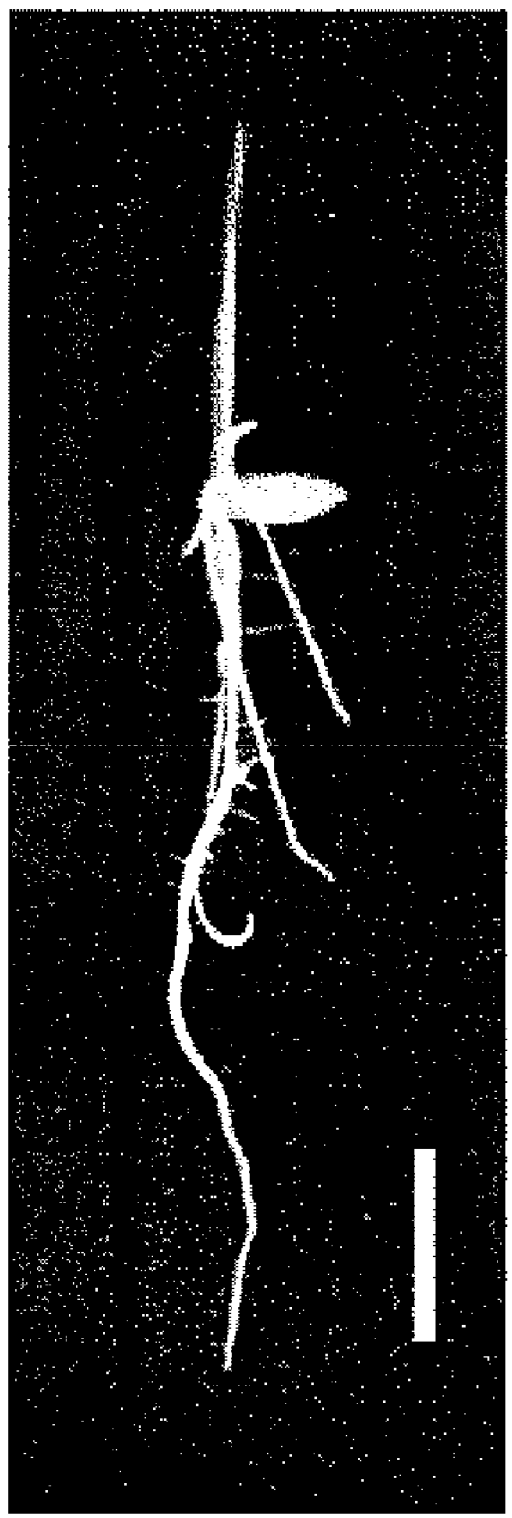

[Fig.11]
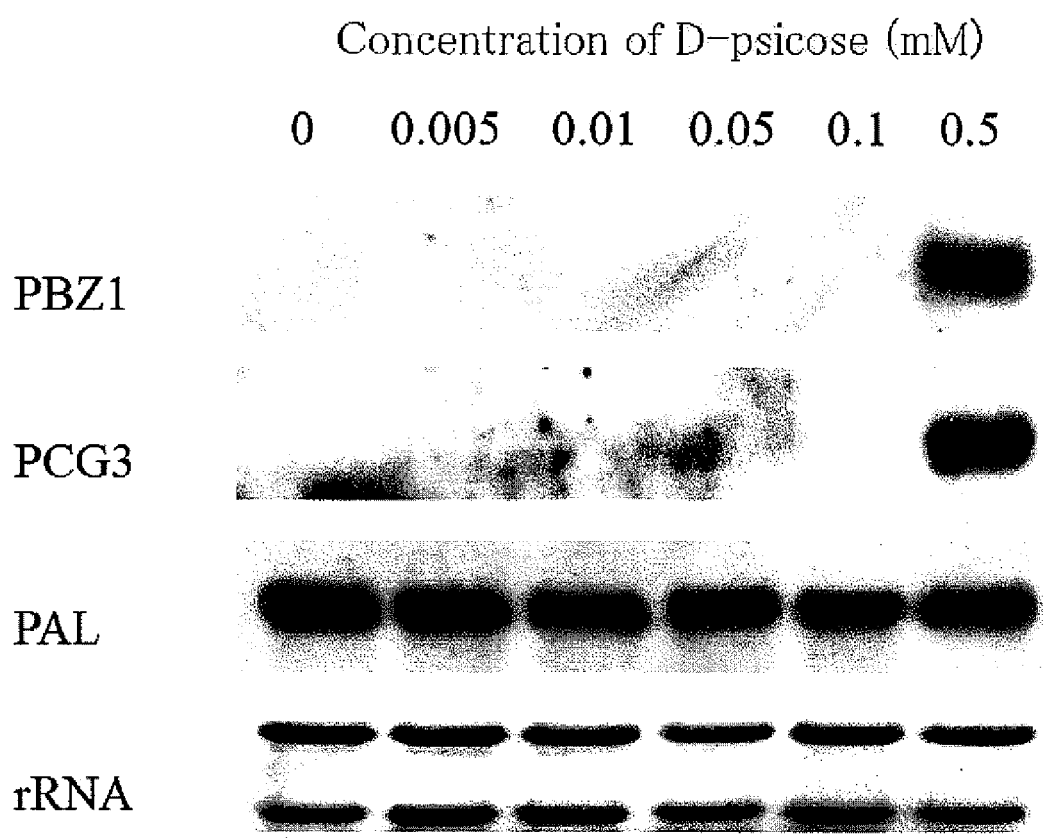

[Fig.12]
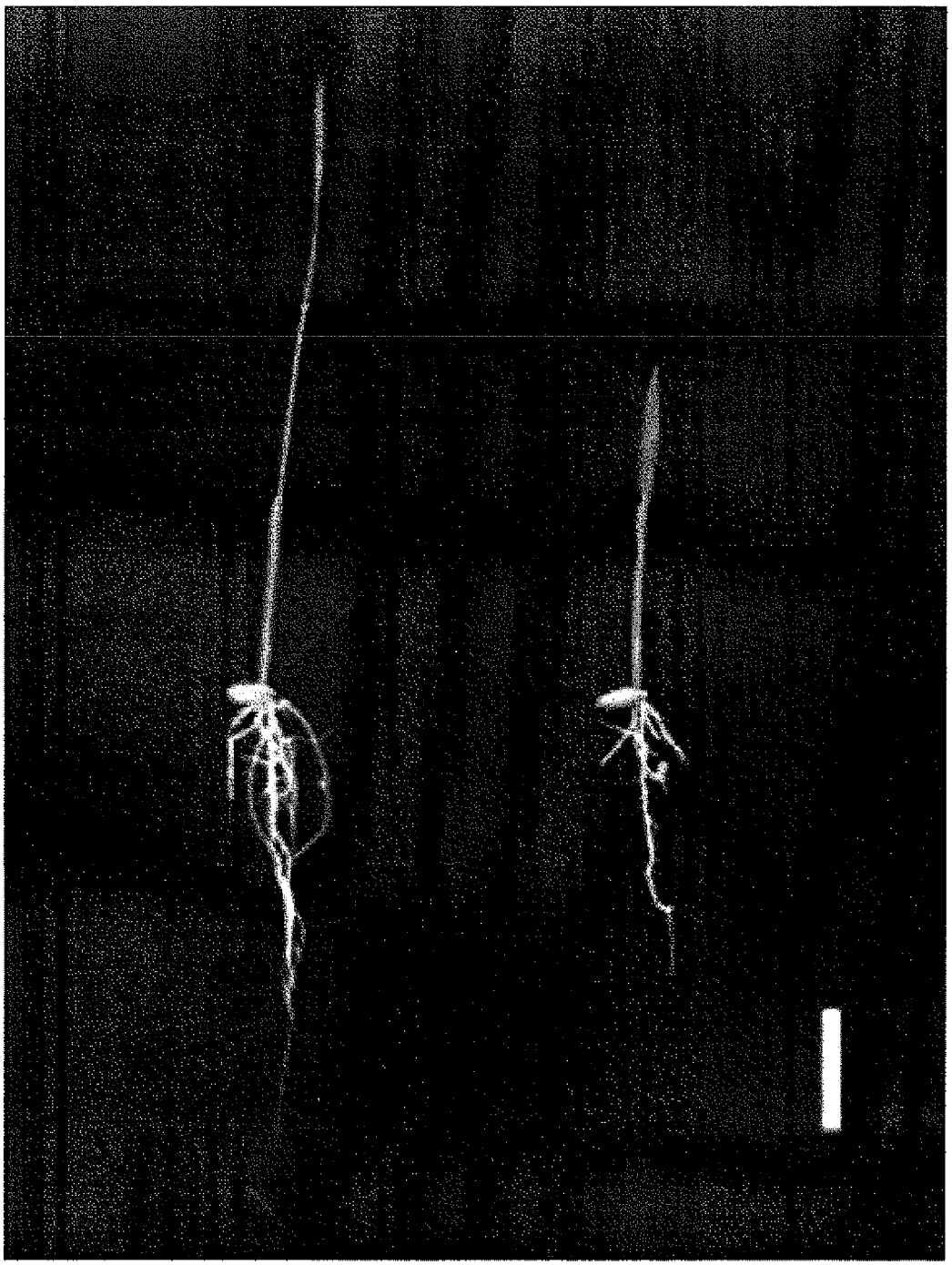

[Fig.13]
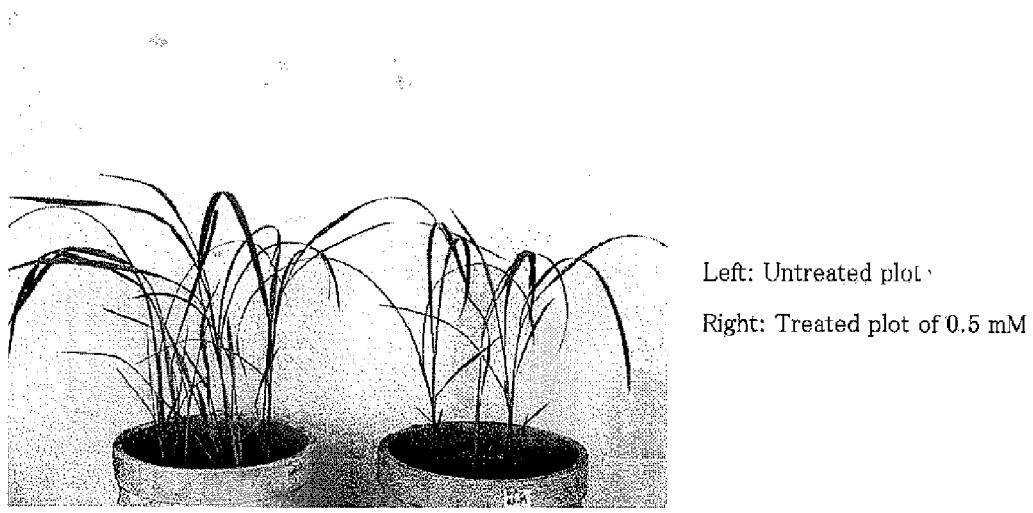
Left: Untreated plot
Right: Treated plot of 0.5 mM
[Fig.14]
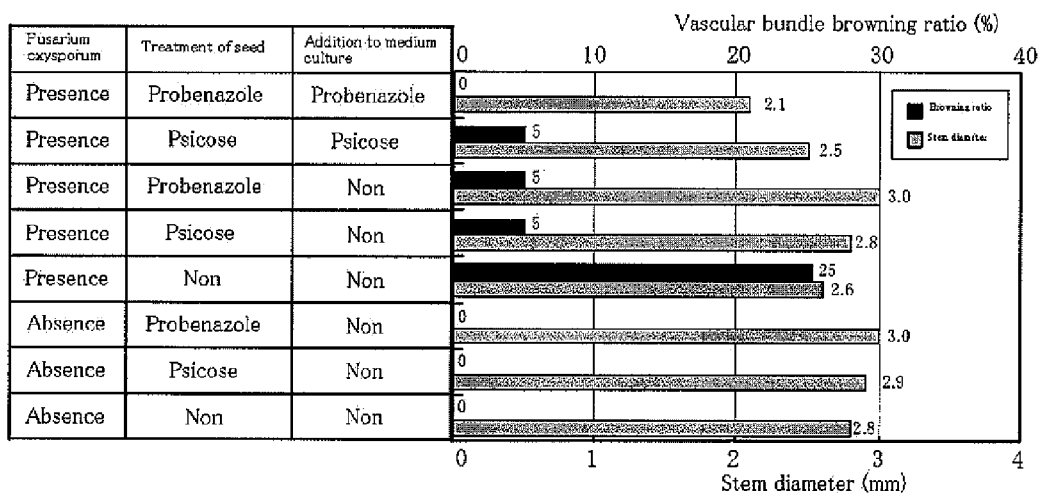

[Fig.15]
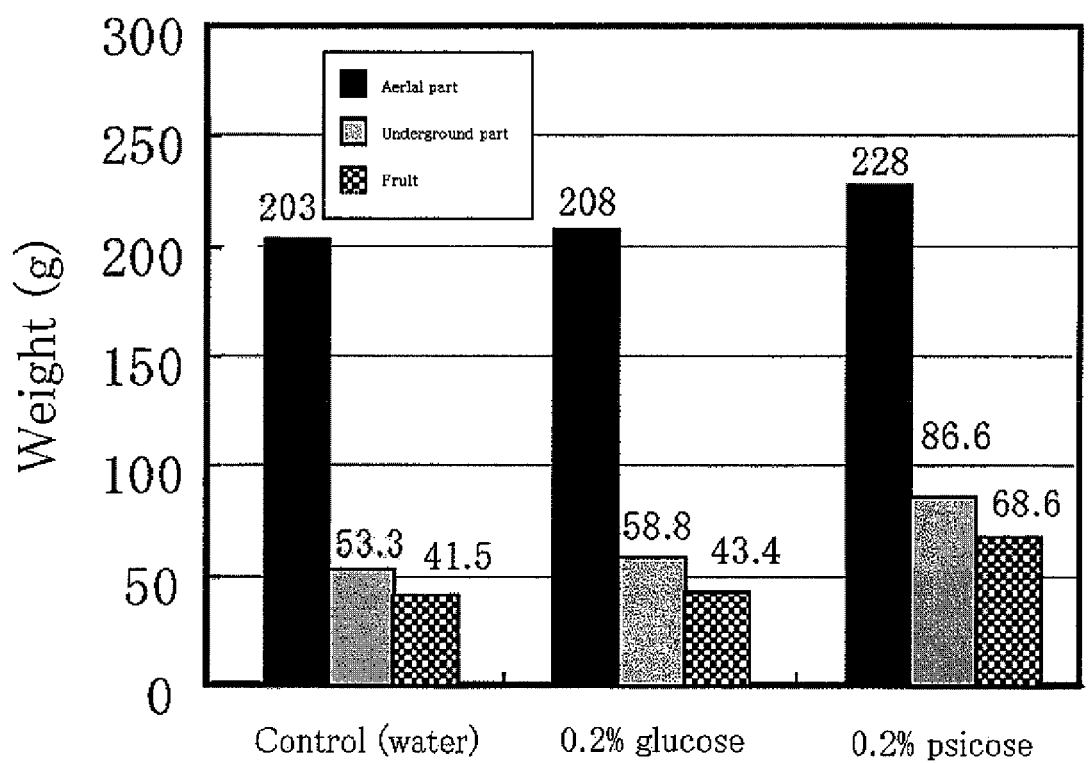

[Fig.16]
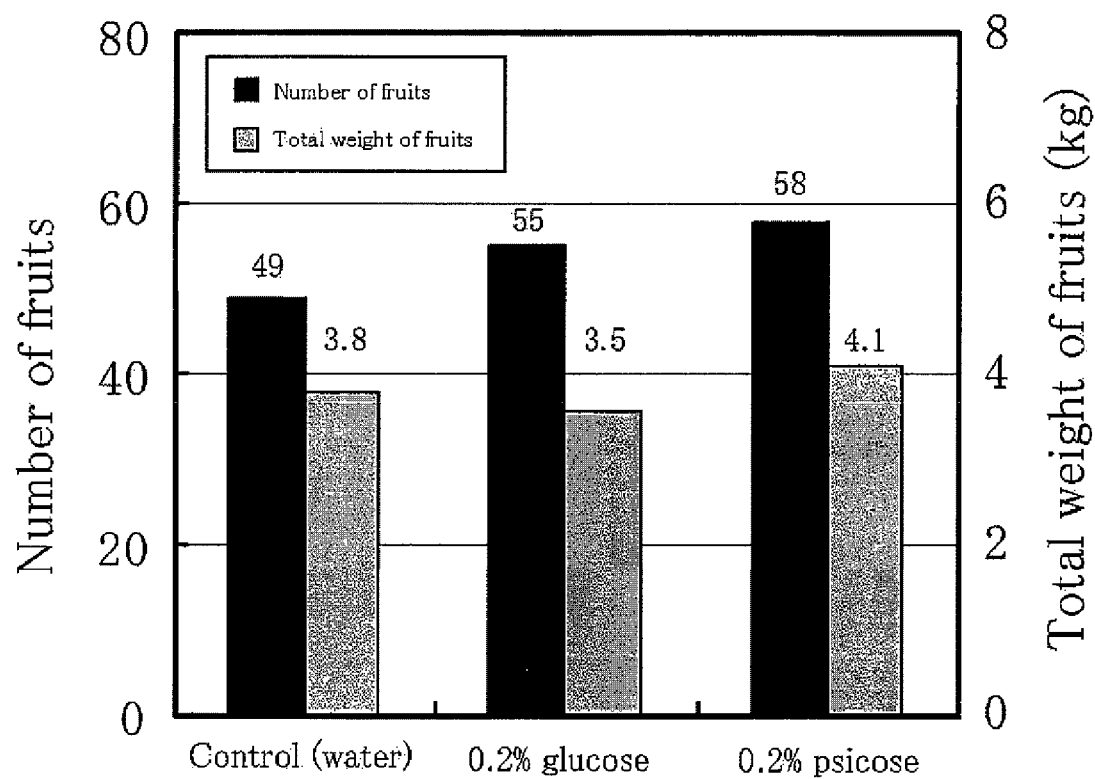

[Fig.17]
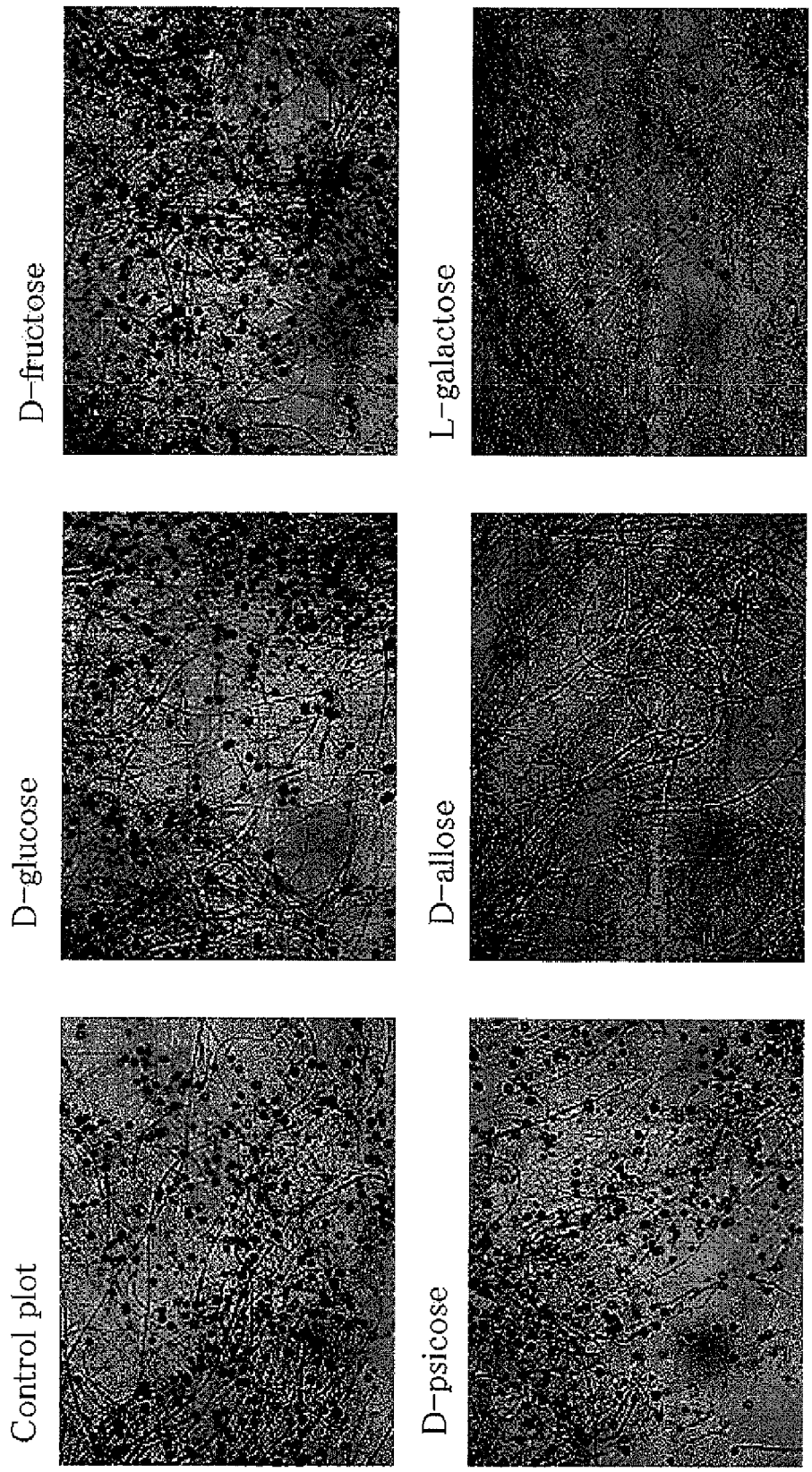

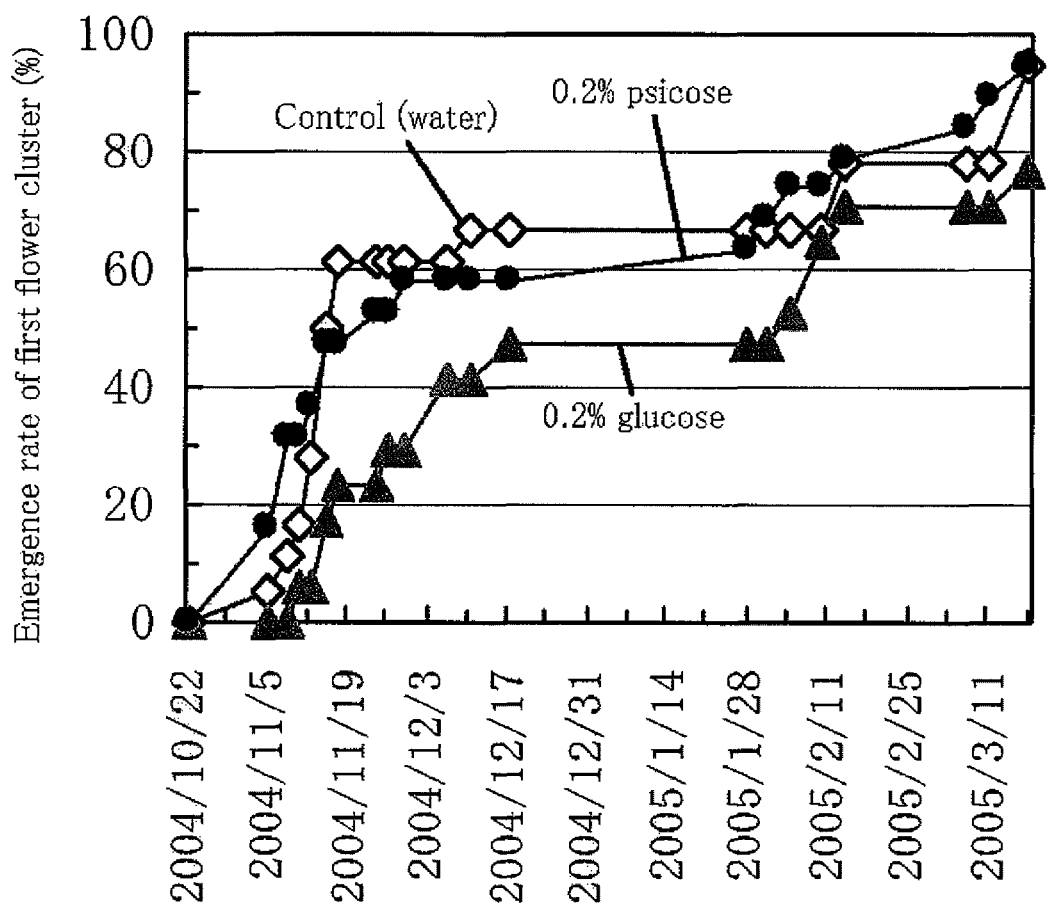
[Fig.18]

[Fig.19]
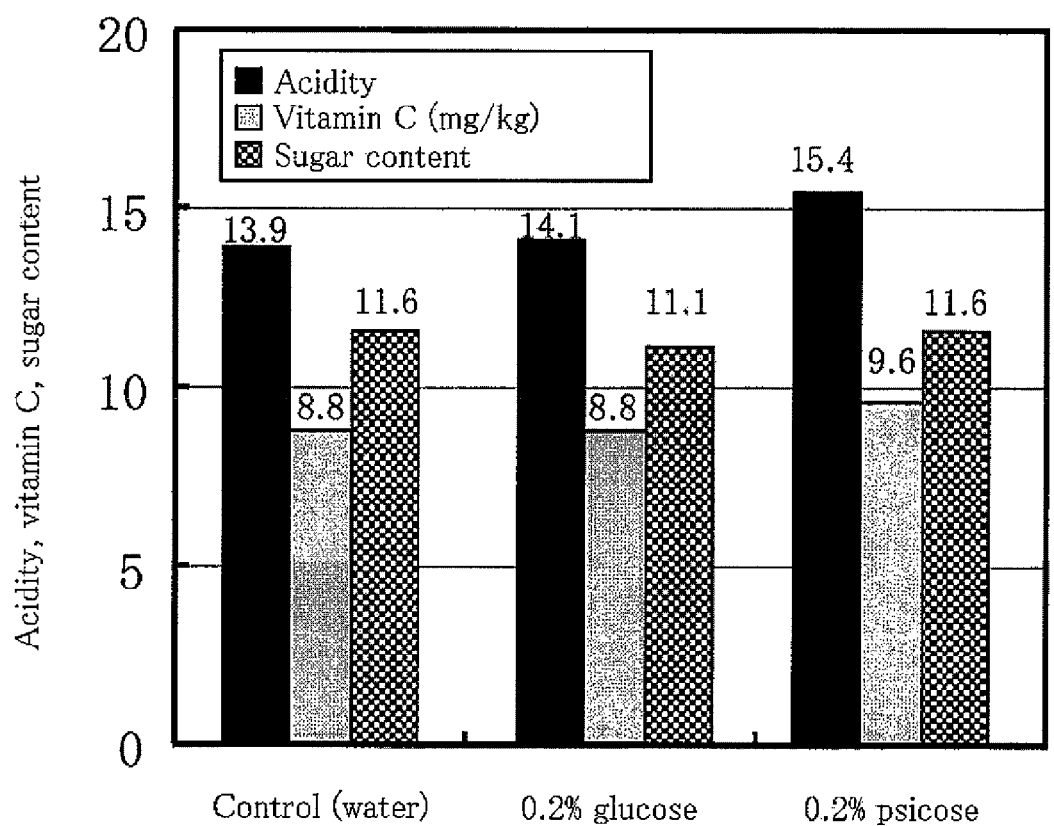

[Fig.20]
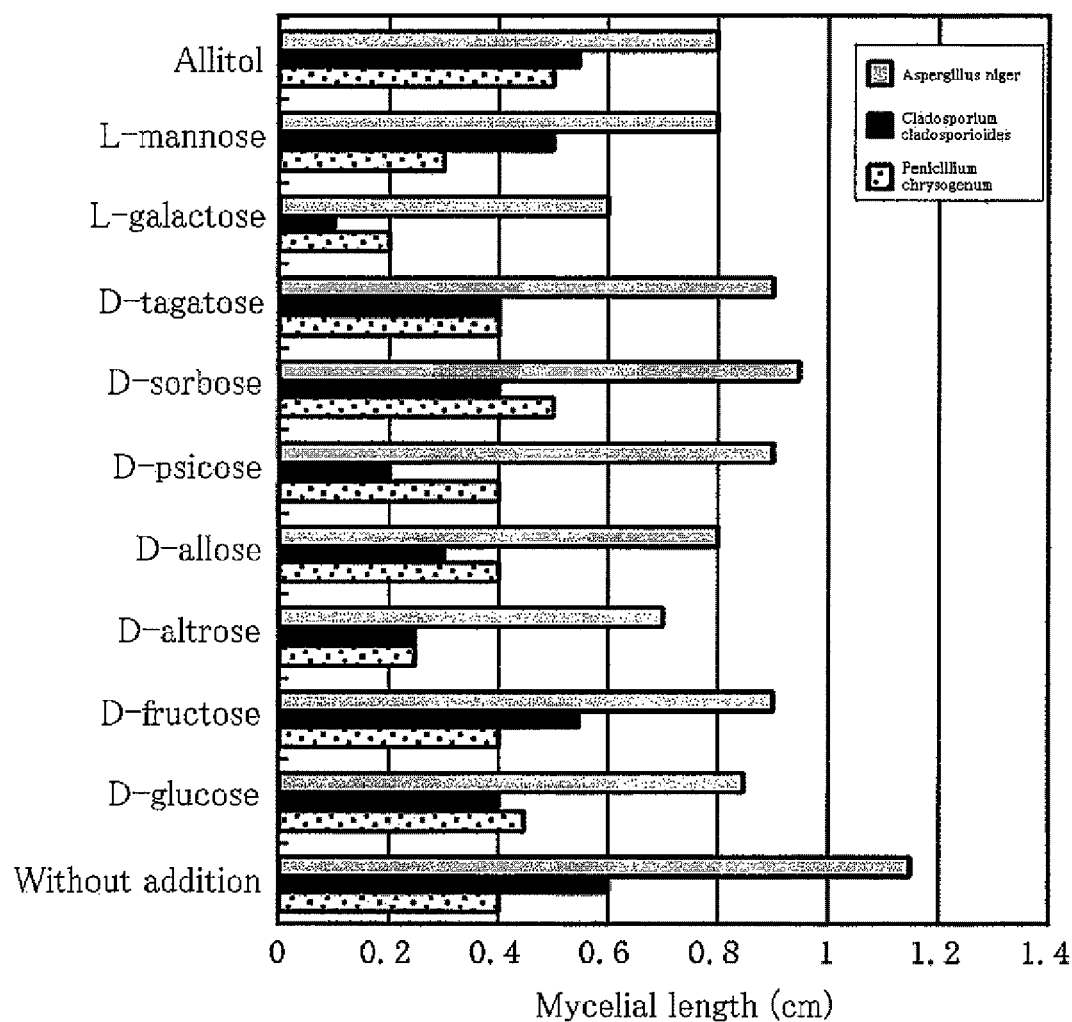

[Fig.21]
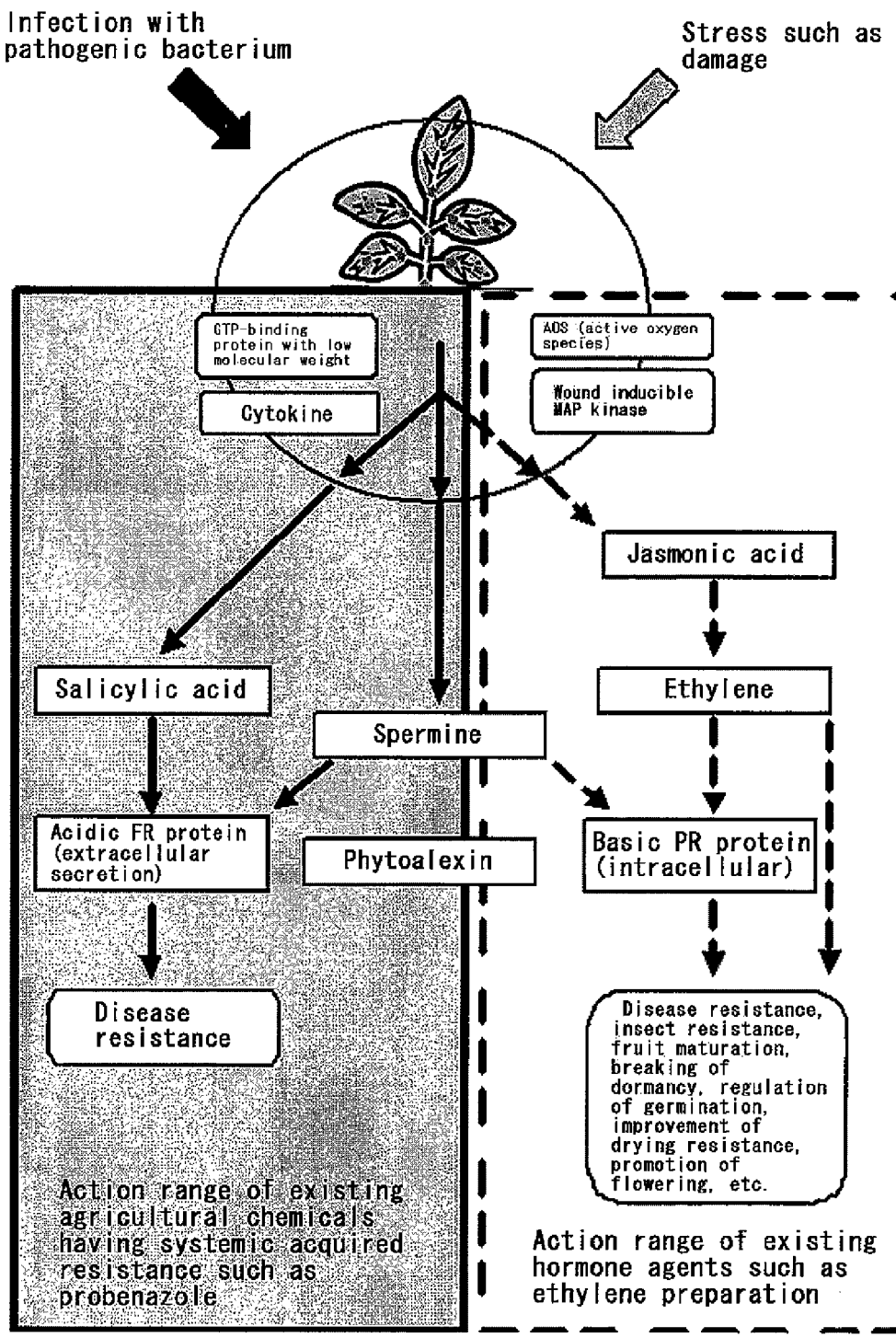

[Fig.22]
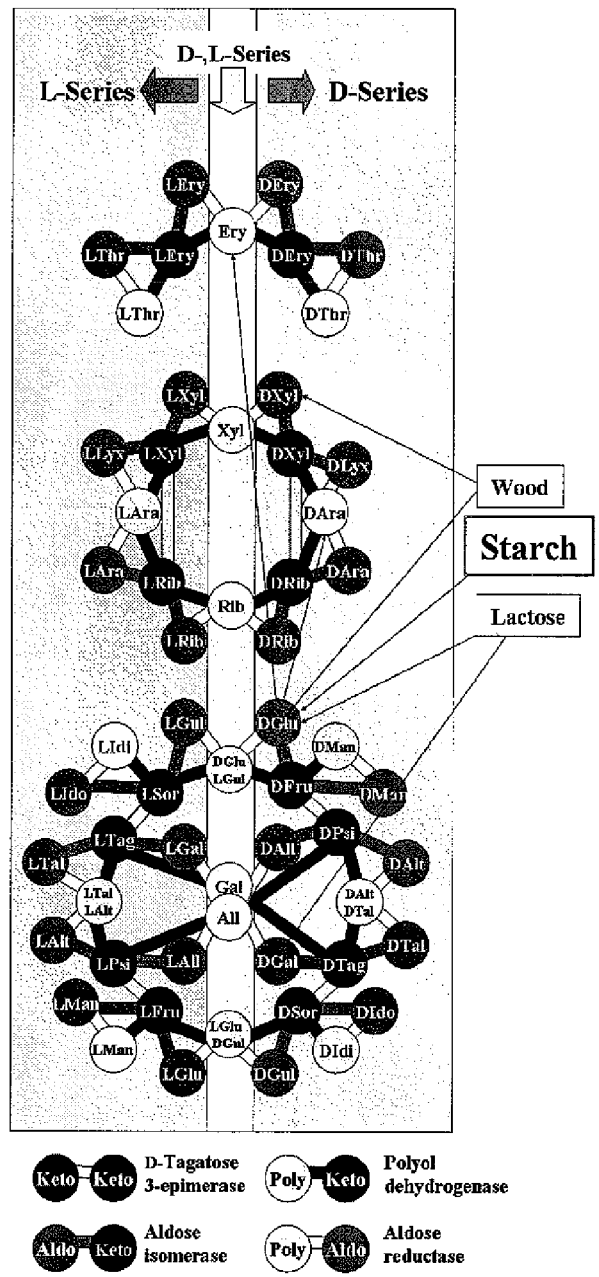

[Fig.23]
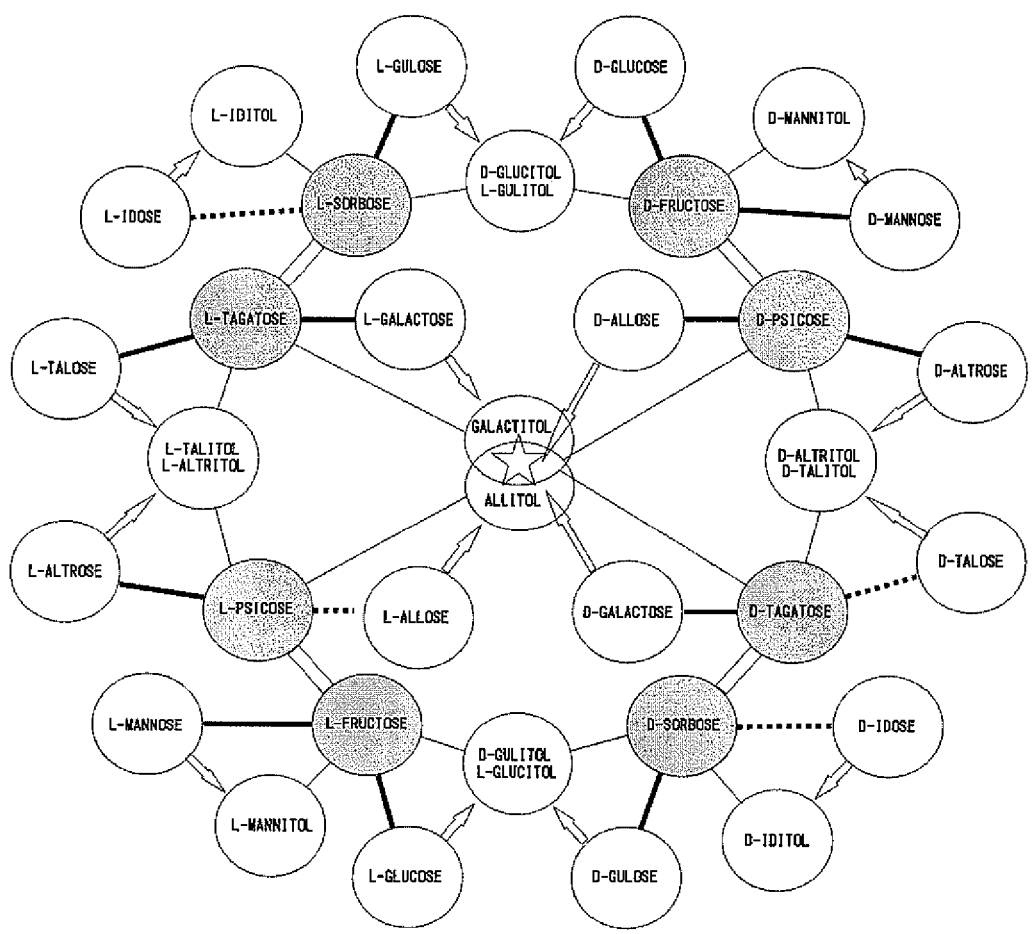

UTILIZATION OF RARE SUGARS IN PLANT OR MICROORGANISM

TECHNICAL FIELD

The present invention relates to utilization of a rare sugar for inducing systemic acquired resistance in a plant, regulating the growth of a plant and inhibiting the growth of a microorganism. More particularly, it relates to utilization of a rare sugar as an agricultural chemical with the use of the effect of inducing systemic acquired resistance in a plant, a plant disease inhibitor, an inducer of a plant growth regulatory factor (i.e., an inducer of plant hormone-like actions consisting of disease resistance, insect resistance, fruit maturation, breaking of dormancy, regulation of germination, drying resistance, and other than this, resistance to environmental stresses such as low temperature resistance, high temperature resistance, salt resistance and heavy metal resistance and promotion of flowering), a plant growth regulator and a microorganism growth inhibitor. When a case of the plant growth regulator is cited as an example, it relates to a method of regulating the growth of a plant in which the plant growth regulator is used by giving it by a method such as foliar spraying thereof in a state of a solution or a solid onto roots, stems, leaves or fruits of the plant, or soil drench.

In the present invention, "plant" represents those which can be recognized from the term "plant" per se, including vegetables, fruits, fruit trees, grains, seeds, bulbs, flowering grasses, herbs, those taxonomically classified as a plant and the like.

BACKGROUND ART

Various nutritional elements are necessary for plants to grow. For example, nitrogen, phosphorus and potassium are known as three macronutrients contained in a fertilizer. Further, as minerals, Ca, Mg, Fe, S, B, Mn, Cu, Zn, Mo, Cl, Si, Na and the like are necessary. These nutritional components such as nitrogen, phosphorus and potassium or minerals are applied in a form of a base fertilizer or an additional fertilizer, or a liquid fertilizer is diluted and the resulting liquid is applied by soil drench or foliar spraying. Further, in plant tissue culture such as production of mericlone plants, they are added as medium components. These components are essential and necessary for plants to grow. However, even if they are applied at a concentration not lower than a certain concentration, they cannot contribute to the improvement of the growth and yield of plants any more.

However, it is an important object in the agricultural production to try to increase the yield by promoting the growth of agricultural crops thereby to increase the crop yield per unit area or to shorten the cultivation period, and various plant growth regulators required for the above object have been developed and used. The plant growth regulators typified by gibberellin, auxin and the like are used for regulating growth and morphogenetic reaction such as germination, rooting, elongation, flowering and fruiting, however, the action of these substances is diverse and complicated, and their use is limited. In order to solve such a problem, a technique in which a foliar spraying agent using an oligosaccharide or a liquid fertilizer containing a sugar, a mineral, an amino acid, a seaweed extract or a microbial fermentation extract is sprayed onto leaves or fertilization is carried out in the form of a solution is known, however, it is not satisfactory in terms of the effect for practical purpose at present.

Further, in the conventional plant growth regulators, an action of promoting the growth of plants are regarded as important, and it is not intended to target an action of inhibiting the growth of plants except for herbicides and the like. However, a technique of appropriately inhibiting the growth of plants in a field of storage of seedlings in preparation for permanent planting or prolongation of life of ornamental plants or the like has been demanded.

On the other hand, in the agricultural production, measures for disease and insect damage are one of the most important issues. In particular, agricultural chemicals have become essential members for the current agriculture for ensuring food production, for example, for the measures for disease and insect damage, the use of such as herbicides for work saving, the use for stabilizing the quality or yield, and so on. However, by considering the use of agricultural chemicals for killing insects and bacteria, their toxicity against humans is high, and they have a risk of having adverse effects on the health of agricultural producers and consumers. With regard to the restriction on the use of agricultural chemicals, the criteria for use and the like are stipulated in the "Agricultural Chemicals Regulation Law", however, the present situation is that among agricultural chemicals which are allowed to be used, there are a number of agricultural chemicals which are suspected to have acute toxicity, chronic toxicity, carcinogenicity, teratogenicity, multigeneration genotoxicity and the like.

Further, recently, agricultural chemical residues in agricultural products have become a big issue. In order to prevent pathogen infection of plants, spraying of a bactericide is generally performed. However, disease protection by the generally performed spraying of an agricultural chemical has a lot of problems related to safety such as effects on the human body due to agricultural chemical residues in crops and contamination in the environment. Further, in terms of the effect of agricultural chemicals, there is a problem that once a pathogen penetrates plants, agricultural chemicals cannot exhibit their bactericidal effect any more. As measures for plant diseases alternative to conventional agricultural chemicals, a protection technique which has high safety and is not harmful to the environment such as pyroligneous acid, bamboo pyroligneous acid, sodium bicarbonate, electrolyzed acid water and the like is known. However, it is not sufficient in terms of the effect and cost, and a technique of inhibiting a plant disease which is safe and has a high effect has been demanded. Further, also in fields other than a plant disease, microbiological control by ethanol, hypochlorous acid, electrolyzed acid water, invert soap or the like has been performed, however, it is not sufficient in terms of irritation to human, safety and the like.

Many of the conventional agricultural chemicals directly targets plant pathogenic bacteria such as filamentous fungi and bacteria or harmful insects, however, there are problems such as effects on the human body or ambient environment due to the toxicity of the agents as described above. Accordingly, as a chemical substance that activates the biological defense mechanism inherent in plants thereby to express disease resistance in the whole plant body, probenazole, acibenzolar-5-methyl or the like is used. Induction of systemic disease resistance by the activation of the biological defense mechanism inherent in plants is called systemic acquired resistance (SAR).

As the agricultural chemical with the use of the induction of systemic acquired resistance in plants, probenazole and the like have been in practical use, and in particular, probenazole has a very large market as a disease inhibitor against *Pyricularia oryzae*. However, there arises a problem that an effect of such an agricultural chemical on diseases other than *Pyricularia oryzae* is small, therefore, a future preparation has been demanded worldwide. Further, a jasmonic acid derivative or an ethylene preparation has been used for the purpose of fruit maturation or promotion of flowering, however, their range of action is limited.

In recent years, many reports have been published that recognition of foreign substances is involved in the activation of a group of resistance genes in plants, and a factor which is recognized as a foreign substance and induces the resistance gene became called an elicitor. That is, in order to prevent pathogen infection of plants, spraying of a bactericide is generally performed. However, when a pathogenic bacterium penetrates plant body, the plant recognizes it and activates the plant defense system such as the synthesis of phytoalexin, which is an antibacterial substance, and defends by itself. A substance that induces such resistance reaction by activating the plant secondary metabolic system is called an elicitor (Patent Documents 4 and 2, and Non-Patent Document 1). The present inventors found that a rare sugar has an action of enhancing disease resistance in a plant and separately applied for a patent (Patent Document 6). That is, it is a phenomenon in which a rare sugar reacts against a plant and a variety of proteins that impart disease resistance in the plant body are produced, and its application as an agent for enhancing a plant activity, an agricultural chemical which is not harmful to the environment or the like is expanded, therefore, it is a basically important study finding. However, because the plant secondary metabolic system is complicated or activation of an enzyme occurs in a short time, the mechanism of activation of plant defense system by the elicitor has hardly been elucidated so far.

A problem caused by the growth of harmful microorganisms has become a critical issue not only in a field of a plant disease, but also in many fields such as processing plants for fresh food such as precut vegetables, food production plants, medical facilities, living environments involving dew formation or the like and air-conditioning equipment involving *Legionella* bacteria. For example, an ethanol preparation to be used for food and in food production environment is a bactericide that inhibits the growth of saprophytic bacteria having an unfavorable effect on food and food production environment, however, many of them are a high concentration ethanol preparation which imparts an unfavorable taste or odor to food, irritates eyes or throat of workers engaged in the production processing work or has an effect on hands or skin, therefore, there is a problem with ensuring the work force. Further, for washing precut vegetables, sodium hypochlorite or electrolyzed strong acid water is used. This method does not cost much and has a bactericidal activity, therefore, it is widely used. However, because the odor of chlorine remains in the products, when washing with water is carried out again, the expense increases, and further, there is a concern about atopic dermatitis caused by chlorine and carcinogenicity. Although at present, a demand for precut vegetables is expanded, an edible washing up liquid free of agricultural chemicals, which responds to the needs of consumers, cannot be found.

Patent Document 1: JP-A-8-225404
Patent Document 2: JP-A-2000-319107
Patent Document 3: JP-A-2000-44404
Patent Document 4: JP-A-7-67681
Patent Document 5: JP-A-7-10901
Patent Document 6: JP-A-2004-300079
Non-Patent Document 1: Plant Cell Technology, Vol. 2, Supplement 1, p. 399, 1990

DISCLOSURE OF THE INVENTION

Problems that the Invention is to Solve

The disease protection by spraying of an agricultural chemical generally performed has a lot of problems related to safety such as effects on the human body due to agricultural chemical residues in crops and contamination in the environment. Further, in terms of the effect of agricultural chemicals, there is a problem that once a pathogen penetrates plants, agricultural chemicals cannot exhibit their bactericidal effect any more. In this way, conventional agricultural chemicals have been strongly pointed out in terms of its safety and the like. The present invention has its object to provide an agricultural chemical with the use of an effect of inducing systemic acquired resistance in a plant, which can remarkably reduce the amount of the agricultural chemical to be used, a plant disease inhibitor, an inducer of a plant growth regulatory factor and a microorganism growth inhibitor, and a method of using a rare sugar using the same.

Further, the present invention has its object to provide a growth inhibitor of a harmful microorganism as well as a plant pathogenic bacterium and a method of inhibiting the growth of a microorganism. That is, an object of the present invention is to provide a microorganism growth inhibitor which inhibits the growth of saprophytic bacteria having an unfavorable effect on food production processing, medical facilities, living environments, air-conditioning equipment or the like, does not impart an unfavorable taste or odor, and is safe and harmless to human, a method of inhibiting the growth of a microorganism.

For the purpose of increasing the crop yield, a large amount of fertilizer is applied to the soil, therefore, various elements in the soil turned out to be excessive, whereby the balance of absorption thereof is disrupted, or growth stagnation of plants or the like occurs, and problems arise that an objective increase in the yield cannot be achieved, the quality such as sugar content or freshness is not improved and the like.

Further, because there is also a limitation on absorption of roots for aiming at absorption of nutrients, absorption directly from leaves or fruits has been tried by spraying an aqueous solution or an aqueous suspension of essential fertilizer elements. However, even if an aqueous solution of essential elements is only sprayed onto leaves, there is a problem in terms of the absorption efficiency. On the contrary, by spraying excessive fertilizer components, a stress is imposed on the plant, whereby damage is caused.

Further, in order to appropriately inhibit the growth of plants without causing any damage, storage of the plants at a low temperature or the like has been carried out, however, a means using an agent is not sufficient.

The present invention has its object to provide a plant growth regulator, a composition of the plant growth regulator, or a method of regulating the growth of a plant in which either of the plant growth regulator and the composition of the plant growth regulator is used by giving it by a method such as foliar spraying thereof in a state of a solution or a solid onto roots, stems, leaves or fruits of the plant, immersion of a cutting base in a solution or soil drench.

Means for Solving the Problems

That is, a gist of the present invention is a composition comprising a rare sugar as an active ingredient according to any of the following (1) to (13).

(1) A composition comprising a rare sugar as an active ingredient, which has an effect of inducing systemic acquired resistance in a plant.

(2) The composition according to (1), wherein the composition is an inducer of systemic acquired resistance.

(3) The composition according to (2), wherein the inducer of systemic acquired resistance is an agricultural chemical with the use of an effect of inducing systemic acquired resistance in a plant.

(4) The composition according to (2), wherein the inducer of systemic acquired resistance is a plant disease inhibitor.

(5) The composition according to (2), wherein the inducer of systemic acquired resistance is an inducer of a plant growth regulatory factor.

(6) The composition according to (5), wherein the plant growth regulatory factor is selected from the group of plant hormone-like actions consisting of disease resistance, insect resistance, fruit maturation, breaking of dormancy, regulation of germination, drying resistance, and other than this, resistance to environmental stresses such as low temperature resistance, high temperature resistance, salt resistance and heavy metal resistance and promotion of flowering.

(7) A composition comprising a rare sugar as an active ingredient, which has an effect of regulating the growth of a plant based on an action of promoting or inhibiting the growth thereof.

(8) The composition according to (7), wherein the composition is a plant growth regulator.

(9) A composition comprising a rare sugar as an active ingredient, which has an effect of inhibiting the growth of a microorganism.

(10) The composition according to (9), which is a microorganism growth inhibitor.

(11) The composition according to any one of (1) to (10), wherein the rare sugar is an aldose or a ketose.

(12) The composition according to (11), wherein the ketose is D-psicose or a mixture of D-psicose and D-fructose.

(13) The composition according to (11), wherein the aldose is D-allose, D-altrose or L-galactose.

A gist of the present invention is a method of using a rare sugar according to any of the following (14) to (25).

(14) A method of using a rare sugar, characterized in that the rare sugar is used for a plant to induce systemic acquired resistance.

(15) The method of using a rare sugar according to (14), wherein the induction of systemic acquired resistance is induction of an agricultural chemical action with the use of an effect of inducing systemic acquired resistance.

(16) The method of using a rare sugar according to (14), wherein the induction of systemic acquired resistance is induction of inhibition of a plant disease.

(17) The method of using a rare sugar according to (14), wherein the induction of systemic acquired resistance is induction of a plant growth regulatory factor.

(18) The method of using a rare sugar according to (17), wherein the plant growth regulatory factor is selected from the group of plant hormone-like actions consisting of disease resistance, insect resistance, fruit maturation, breaking of dormancy, regulation of germination, drying resistance, and other than this, resistance to environmental stresses such as low temperature resistance, high temperature resistance, salt resistance and heavy metal resistance and promotion of flowering.

(19) A method of using a rare sugar, characterized in that the rare sugar is used for a plant to regulate the growth of the plant based on an action of promoting or inhibiting the growth thereof.

(20) The method of using a rare sugar according to (19), wherein the rare sugar is used as a plant growth regulator.

(21) A method of using a rare sugar, characterized in that the rare sugar is used for a microorganism to inhibit the growth thereof.

(22) The method of using a rare sugar according to (21), wherein the rare sugar is used as a microorganism growth inhibitor.

(23) The method of using a rare sugar according to any one of (14) to (22), wherein the rare sugar is an aldose or a ketose.

(24) The method of using a rare sugar according to (23), wherein the ketose is D-psicose or a mixture of D-psicose and D-fructose.

(25) The method of using a rare sugar according to (23), wherein the aldose is D-allose, D-altrose or L-galactose.

Advantage of the Invention

The present invention shows that a rare sugar such as D-psicose induces systemic acquired resistance. Its effect is not only improvement of disease resistance induced by such as probenazole but also improvement of resistance to an environmental stress such as a low temperature stress or a drying stress. By using the rare sugar, systemic acquired resistance can be induced, and not only disease resistance but also resistance to a resistance to various stresses can be improved. The rare sugar has very low toxicity and is easily degraded in nature, therefore, it can be used as an inducer of systemic acquired resistance which has high safety and is not harmful to the environment.

The present invention can provide a plant disease inhibitor or a composition of the plant disease inhibitor, which may remarkably reduce the amount of an agricultural chemical to be used, or a method of inhibiting a plant disease in which either of the plant disease inhibitor and the composition of the plant disease inhibitor is used by giving it by a method such as foliar spraying thereof in a state of a solution or a solid onto roots, stems, leaves or fruits of the plant or soil drench.

The present invention can provide a plant growth regulator, a composition of the plant growth regulator, or a method of regulating the growth of a plant in which either of the plant growth regulator and the composition of the plant growth regulator is used by giving it by a method such as foliar spraying thereof in a state of a solution or a solid onto roots, stems, leaves or fruits of the plant, immersion of a cutting base in a solution or soil drench.

While D-psicose or D-allose at a high concentration inhibits the growth of plants, a case in which D-psicose or D-allose at a low concentration promotes the growth on the contrary to this is often observed, which is a notable effect of such a rare sugar.

Further, the present invention can provide a growth inhibitor of a harmful microorganism or a method of inhibiting the growth of a microorganism as well as an effect on a plant such as a plant pathogenic bacterium, which is used in fields of such as food production processing, medical facilities, living environments, air-conditioning equipment or the like. It can provide the microorganism growth inhibitor which inhibits the growth of saprophytic bacteria having an unfavorable effect on food production processing, medical facilities, living environments, air-conditioning equipment or the like, does not impart an unfavorable taste or odor, and is safe and harmless to human or a method of inhibiting the growth of a microorganism using the same.

BEST MODE FOR CARRYING OUT THE INVENTION

In the present invention, "plant" represents those which can be recognized from the term "plant" per se, including vegetables, fruits, fruit trees, grains, seeds, bulbs, flowering grasses, herbs, those taxonomically classified as a plant and the like.

Further, a microorganism which becomes a target of growth inhibition by a rare sugar includes not only plant pathogenic bacteria, but also harmful microorganisms, that is, saprophytic bacteria having an unfavorable effect on food production processing, medical facilities, living environments, air-conditioning equipment and the like.

The rare sugar will be described. The "rare sugar" can be defined as a monosaccharide that exists only in a small amount in nature. There are 7 types of monosaccharides that exist in a large amount in nature, which are D-glucose, D-fructose, D-galactose, D-mannose, D-ribose, D-xylose and L-arabinose, and the other monosaccharides exist in a small amount in nature and can be classified into a rare sugar. Further, a sugar alcohol can be produced by reducing a monosaccharide, and D-sorbitol and D-mannitol exist in a relatively large amount in nature, however, the other sugar alcohols exist in a small amount, therefore, these can also be defined as a rare sugar in accordance with the present invention. It has been difficult to obtain such a rare sugar so far, however, a process for producing a rare sugar from a monosaccharide that exists in a large amount in nature is being developed, and it can be produced by utilizing the technique.

Hereinafter, description based on Izumoring proposed in order to more easily understand a correlation of these monosaccharides will be added (see WO 03/097820).

A linkage diagram in which all the monosaccharides having 4 to 6 carbon atoms are linked together based on their production processes and molecular structures (D-form and L-form) shown in FIG. 22 is the overall diagram of Izumoring (registered trademark, hereinafter omitted). That is, what one can understand from FIG. 22 is that monosaccharides having 4, 5 and 6 carbon atoms are all linked together. In the overall diagram, the members in Izumoring of C6 are linked together, the members in Izumoring of C5 are linked together, the members in Izumoring of C4 are linked together, and Izumorings of C4, C5 and C6 are all linked together. This concept is important. In order to reduce the number of carbon atoms, a fermentation method is mainly used. It is characterized by being a big linkage diagram in which all the monosaccharides having different number of carbon atoms are linked together.

In Izumoring of the monosaccharides having 6 carbon atoms (hexoses), as shown in the lower portion of FIG. 22 and FIG. 23, there are a total of 34 types of monosaccharides having 6 carbon atoms (hexoses) including 16 types of aldoses, 8 types of ketoses and 10 types of sugar alcohols. It is known by the studies including the studies performed by the present inventors that these sugars can be converted by an oxidoreductase reaction, an aldose isomerization reaction or an aldose reductase reaction.

However, the upper group, the middle group and the lower group were not linked together by an enzymatic reaction in the conventional studies. In other words, although D-glucose (glucose) or D-fructose belonging to the upper group is a sugar that exists in a large amount in nature and is inexpensive, a rare sugar could not be synthesized from this sugar. However, in the process of the study performed by the present inventors, an enzyme that links these was found. D-sorbose which was completely unexpectedly found in a culture solution of a bacterium having an enzyme that synthesizes D-tagatose from galactitol, which was the beginning of the finding of the enzyme. From the results of investigating the cause, it was found that this bacterium produces an enzyme called D-tagatose-3-epimerase (DTE).

As shown in the lower portion of FIG. 22 and FIG. 23, it is understood that this DTE is an enzyme that connects between D-tagatose and D-sorbose which was disconnected so far. Further surprisingly, it was found that this DTE is an enzyme that epimerizes all ketoses at the C-3 position, and is a unique enzyme having an extremely broad substrate specificity so as to act on D-fructose and D-psicose, L-sorbose and L-tagatose, D-tagatose and D-sorbose, L-psicose and L-fructose, which could not be synthetically connected so far. Because of the finding of this DTE, all the monosaccharides are linked together in a ring, and structuring of the knowledge of monosaccharides is completed, which was named Izumoring.

When taking a close look at FIG. 23, it is found that there are L-forms at the left side, D-forms at the right side and DL-forms in the middle, and further L-forms and D-forms are symmetric with respect to the central point (asterisk) of the ring. For example, D-glucose and L-glucose are symmetric with respect to the central point. Further, the value of Izumoring is that it becomes a plan diagram for production of all the monosaccharides. In the previous example, if L-glucose is intended to be produced from D-glucose as a starting material, it is indicated that D-glucose is isomerized, epimerized, reduced, oxidized, epimerized and isomerized, whereby L-glucose can be produced.

By using Izumoring of monosaccharides having 6 carbon atoms (hexoses), the correlation between sugars that exist in a large amount in nature and rare sugars that exist only in a small amount in nature is shown. D-glucose, D-fructose, D-mannose and D-galactose that can be produced from lactose in milk exist in a large amount in nature, and the other sugars are classified into a rare sugar that exists only in a small amount in nature. Because of the finding of DTE, D-fructose and D-psicose are produced from D-glucose, and further it became possible to produce D-allose, allitol and D-talitol.

When the meanings of Izumoring of monosaccharides having 6 carbon atoms (hexoses) are summarized, they include as follows. Based on the production process and molecular structure (D-form and L-form), all the monosaccharides are put in order structurally (structuring of knowledge), whereby the overall picture of monosaccharides can be understood; an effective and efficient approach for study can be selected; the optimum production pathway can be designed; and a missing portion can be predicted.

D-glucose in Izumoring of C6 is linked to D-arabitol in Izumoring of C5 and erythritol in Izumoring of C4. These lines indicate that D-arabitol and erythritol can be produced from D-glucose by a fermentation method. That is, Izumoring of C6, Izumoring of C5 and Izumoring of C4 are linked together. This linkage is a reaction of decreasing the carbon number by a mainly fermentation method, and it is possible to link Izumoring of C6 to Izumoring of C5 or C4 by a fermentation method other than these two conversion reactions into D-arabitol and erythritol. For example, it is possible to produce D-ribose from D-glucose. As described above, by the three Izumorings, all the monosaccharides having 4, 5 and 6 carbon atoms (aldoses, ketoses and sugar alcohols) are linked together, therefore the location of each monosaccharide in the overall monosaccharides can be clearly identified.

It can be clearly identified that the most famous xylitol can be easily produced by reducing D-xylose that can be produced from wood material of an unused resource. In the case where a large amount of a specific monosaccharide is obtained by a biological reaction, it is possible to easily find the possibility of conversion into a new monosaccharide using it as a raw material. That is, since the location of all the monosaccharides as a raw material can be surely identified from this overall picture, a useful application method can be designed. In particular, an application method can be easily deduced when a monosaccharide is obtained from a waste material or a by-product. It exhibits effectiveness not only in a field of producing a rare sugar, but also in a study of a search for a physiological activity possessed by a rare sugar. For example, when a physiological activity of a certain rare sugar was found, the location of the rare sugar in the linkage diagram shown in FIG. 22 is identified. Then, the comparison with a physiological activity of a rare sugar having a similar structure or the examination of a physiological activity of a rare sugar having a mirror image relationship structurally will help you deduce the mechanism of the physiological activity from the structure of the molecule. Further, by analyzing physiological functions of rare sugars and integrating the properties into Izumoring, it is expected that all the monosaccharides can be put to good use to comprehensively understand the "structure of monosaccharide", "production process for monosaccharide" and "physiological function of monosaccharide" instead of the conventional simple enumerative understanding.

The linkage diagram in which all the monosaccharides having 4 to 6 carbon atoms are linked together is the overall diagram (FIG. 22) of Izumoring, and it can be understood that monosaccharides having 4, 5 and 6 carbon atoms are all linked together. In the overall diagram, the members in Izumoring of C6 are linked together, the members in Izumoring of C5 are linked together, the members in Izumoring of C4 are linked together, and Izumorings of C4, C5 and C6 are all linked together. For example, in Izumoring of the monosaccharides having 6 carbon atoms (hexoses), as shown in the lower portion of FIG. 22 and FIG. 23, there are a total of 34 types of monosaccharides having 6 carbon atoms (hexoses) including 16 types of aldoses, 8 types of ketoses and 10 types of sugar alcohols.

Among rare sugars, a rare sugar called D-psicose which can be produced on a large scale at present will be described. Psicose is one of the hexoses having a ketone group among monosaccharides. It is known that this psicose exists as optical isomers in D-form and L-form. Here, although D-psicose is a known substance, it rarely exists in nature, therefore, it is defined as a "rare sugar" according to the definition of International Society of Rare Sugars. D-psicose is the D-form of psicose classified into a ketose and is a hexose (C6H12O6). Such D-psicose may be obtained by any means including one extracted from nature, one synthesized by a chemical or biological synthesis method and the like. In a relatively easy way, for example, one prepared by a method using epimerase (e.g., see JP-A-6-125776) can be employed. The obtained D-psicose liquid can be purified by a method such as deproteinization, decoloration or demineralization as needed, and then the resulting liquid is concentrated, whereby a D-psicose product in a syrup form can be collected. Further, by carrying out fractionation and purification by column chromatography, a product with a high purity of 99% or higher can be easily obtained. Such D-psicose can be used as a monosaccharide as it is, and also it is expected to be used as a variety of derivatives according to need.

Then, D-allose will be described. D-allose is a rare sugar which was particularly found to have various physiological activities in the study of rare sugars. D-allose (D-allohexose) is the D-form of allose classified into an aldose (aldohexose) and is a hexose (C6H12O6) having a melting point of 178° C. As a process for producing this D-allose, there are a production process by a method of reducing D-allonic acid lactone with sodium amalgam and a production process of synthesizing D-allose from D-psicose by using L-rhamnose isomerase, as described in Shakhawat Hossain Bhuiyan et al., "Journal of Fermentation and Bioengineering", Vol. 85, pp. 539 to 541 (1993). Further recently, it is described in JP-A-2002-17392. A process for producing D-allose from D-psicose by allowing D-xylose isomerase to act on a solution containing D-psicose has been invented. According to the production process described in JP-A-2002-17392, in the case of producing D-allose, it is obtained as an enzymatic reaction liquid containing newly produced D-allose along with unreacted D-psicose.

The type of enzyme to be used in the conversion of a substrate that can be converted into D-allose into D-allose by the enzymatic reaction is not limited, however, an enzyme "L-rhamnose isomerase" that can produce D-allose from D-psicose is exemplified as a preferred enzyme. L-rhamnose isomerase is a known enzyme published in "Journal of Fermentation and Bioengineering", Vol. 85, pp. 539 to 541 (1998). It is an enzyme catalyzing an isomerization reaction from L-rhamnose to L-rhamnulose and an isomerization reaction from L-rhamnulose to L-rhamnose. Because L-rhamnose isomerase also acts on isomerization between D-allose and D-psicose, it is an enzyme that can produce D-allose from D-psicose.

An effect of containing a rare sugar as an active ingredient on induction of systemic acquired resistance in a plant will be described.

Induction of systemic disease resistance by the activation of the biological defense mechanism inherent in plants is called systemic acquired resistance (SAR). The induction of systemic acquired resistance basically refers to a phenomenon in which when some kind of stress is imposed on a part of a plant body, the information is transferred to the whole body and new resistance to the stress is induced in the whole body. The detailed mechanism of induction of systemic acquired resistance has not been made clear yet, however, in general, after a plant pathogenic bacterium or an elicitor substance (a general term of substances that induce a biological defense reaction of plants) is recognized by a plant, generation of active oxygen or signal transduction mediated by salicylic acid, spermine or the like occurs, and then, a PR protein (a specific protein induced after infection) is generated, and so on, whereby systemic acquired resistance is acquired (FIG. 21, Mechanism of induction of systemic acquired resistance in plant). A general inducer of systemic acquired resistance such as probenazole is considered to induce this reaction. On the other hand, when a plant receives a stress such as damage, signal transduction mediated by jasmonic acid or ethylene occurs, which causes not only improvement of disease resistance, but also improvement of insect resistance, fruit maturation, promotion of flowering, breaking of dormancy, regulation of germination, improvement of resistance to stresses such as drying and the like (FIG. 21).

The present invention is based on the fact that a rare sugar such as D-psicose exhibits induction of systemic acquired resistance. The effect of inducing systemic acquired resistance includes not only improvement of disease resistance induced by such as probenazole, but also improvement of resistance to an environmental stress such as a low temperature stress and a drying stress (see FIG. 1). Therefore, by utilizing a rare sugar, systemic acquired resistance can be induced, and not only disease resistance, but also resistance to resistance to a variety of stresses can be improved. The rare sugar has very low toxicity and is easily degraded in nature, therefore, it can be used as an inducer of systemic acquired resistance which has high safety and is not harmful to the environment. More specifically, it can be used as an agricultural chemical with the use of an effect of inducing systemic acquired resistance in a plant, a plant disease inhibitor, an inducer of a plant growth regulatory factor (i.e., an inducer of plant hormone-like actions consisting of disease resistance, insect resistance, fruit maturation, breaking of dormancy, regulation of germination, drying resistance, and other than this, resistance to environmental stresses such as low temperature resistance, high temperature resistance, salt resistance and heavy metal resistance and promotion of flowering), and a microorganism growth inhibitor.

An action of inhibiting a plant disease, which is one of the effects of a rare sugar on induction of systemic acquired resistance, will be described.

Almost all the organic compounds that exist on earth at present are produced by living organisms. From this fact, it is considered that a rare sugar that exists in a small amount in nature is an organic compound that a living organism has low ability to synthesize and degrade. However, there is only a slight difference in the structure of a monosaccharide that exists in a large amount in nature.

Therefore, it is expected that when a living organism comes into contact with a rare sugar, it exhibits a totally unexpected reaction. The present inventors found a completely new reaction of a plant which is a higher organism to a rare sugar and separately applied for a patent (see Patent Document 6). In the Examples of this application, the possibility of promoting an increase in resistance to a pathogenic bacterium or a pathogenic insect by activating a plant pathogenic bacterium or stress response gene pathway by D-psicose is shown. Although a rare sugar has a similar structure to that of a naturally occurring monosaccharide that exists in a large amount in nature, it exists a small amount in nature. Therefore, because the rare sugar is a compound that a plant meets for the very first time in most cases, it is considered that the pathway of metabolism and degradation thereof has not been established and the possibility that the rare sugar is recognized as a foreign substance and the transduction mechanism (stress signaling) of the resistance reaction system is stimulated is high. It is presumed that by testing also other rare sugars using various plants with the use of the same assay as the case of D-psicose, a rare sugar exhibiting an interesting action or having a different action for each plant can be selected and assayed. For example, in an example of a citrus, after a treatment by spraying D-psicose, and other than this, L-psicose, L- & D-tagatose and D-sorbose was carried out, the expression of genes of lipoxygenase and chitinase, which are defense-related genes, was analyzed by Northern blotting, and as a result, among the various rare sugars tested, in the case where the treatment was carried out with D-psicose, induction of the expression of lipoxygenase gene could be maintained for the longest time. This result means that D-psicose plays the most effective role as a factor of stress signaling among the rare sugars that had been tested so far. On the other hand, it has been made clear that D-tagatose strongly induces the expression of chitinase gene, which shows the possibility that a signal transduction pathway induced by a rare sugar exists other than the pathway induced by D-psicose.

The expression of various resistance genes induced by the addition of D-psicose as described above was also confirmed by an experiment using a *Lotus japonicus* cDNA array. In a plant grown by giving 5 mM D-psicose to a medium, a gene group that responds to a variety of pathogenic bacteria and environmental stresses such as genes of chitinase and PR10 protein and genes that responds to a salt stress and a dehydration stress were activated in the first one week. Further, when the concentration of D-psicose in the medium was about 0.1 mM, an increase or a decrease in the expression of a gene group regulated by plant hormones such as auxin was observed rather than the stress response gene group. Therefore, it was predicted that when D-psicose is given to a plant, it has an effect on the expression of a gene group that responds to a variety of pathogenic bacteria and environmental stresses and genes related to plant hormones, and has various effects on the growth of a plant.

The plant to be used as a target in the invention of this application may be any as long as it is a plant that recognizes a rare sugar as a foreign substance and exhibits an action of activating the resistance gene group and promoting an increase in the resistance to a pathogenic bacterium or a pathogenic insect. All the resistance-related genes whose expression was induced by D-psicose in Examples are genes related to a plant defense system common to a wide variety of plant species, and the possibility that a similar action to the action observed in the citrus is exhibited in other plants is high. It was presumed that by performing a test also for various plants with the use of the same assay as that for the citrus, a rare sugar exhibiting an interesting action or having a different action for each plant can be selected and assayed, and the present inventors proceeded further studies, thus the present invention has been achieved.

The present invention relates to a composition of a plant disease inhibitor containing a rare sugar having an inhibitory effect on a plant disease, preferably D-psicose, D-allose, D-altrose or L-galactose. Further, the present invention relates to a method of inhibiting a plant disease comprising supplying any of these plant disease inhibitors or the composition of the plant disease inhibitor to a plant. The form of the plant disease inhibitor of the present invention may be any of a liquid, a paste, a water-dispersible powder, a granule, a powder, a tablet and the like. As a method of supplying the plant disease inhibitor of the present invention to a plant, various means can be employed. For example, a method in which a powder or a granule is sprayed, a diluted aqueous solution is sprayed directly onto a plant such as leaves, stems or fruits, or is injected into the soil, and a method in which it is supplied by diluting and mixing it in a hydroponic culture medium or a feed water which comes into contact with roots in such as hydroponic culture or rockwool can be exemplified.

Examples of the plant that can be treated with the plant disease inhibitor of the present invention include as fruit vegetables, cucumber, pumpkin, watermelon, melon, tomato, egg plant, green pepper, strawberry, okura, green bean, broad bean, pea, green soybean, corn and the like; as leafy vegetables, Chinese cabbage, greens to be pickled, qing-gengcai, cabbage, cauliflower, broccoli, Brussels sprouts, onion, green onion, garlic, shallot, green chive, asparagus, lettuce, Boston lettuce, celery, spinach, crown daisy, parsley, wild chervil, Japanese parsley, udo, Japanese ginger, Japanese butterbur, Japanese basil and the like; as root vegetables, Japanese radish, turnip, burdock, carrot, potato, aroid, sweet potato, yam, ginger, lotus root and the like. Other than these, it can also be used for rice plants, wheat plants, flowering plants and the like.

An action of the inducer of a plant growth regulatory factor, which is one of the effects of a rare sugar on induction of systemic acquired resistance, for example, an action of the inducer of plant hormone-like actions selected from the group consisting of disease resistance, insect resistance, fruit maturation, breaking of dormancy, regulation of germination, drying resistance and promotion of flowering will be described.

It has been made clear that rare sugars, which are each a monosaccharide, have various physiological activities. Effects of these rare sugars on the growth of a plant were examined, and as a result, it was found that a certain rare sugar has an action of growth promotion and another rare sugar exhibits an action of growth inhibition. From now on, by examining an effect of a rare sugar that can be produced on a large scale on growth regulation one by one, diverse activities will be elucidated, and the practical application thereof as a useful growth regulator can be expected.

1) Actions which have been Made Clear so Far

When germinated seedlings of tomato at one week after sowing was treated with a solution obtained by dissolving D-allose in a liquid fertilizer (a mixed liquid of Otsuka No. 1 and No. 2) at different concentrations (0.01 to 5 mM) and raised by hydroponic culture, an action of promoting the growth by 33% in the stem length and 67% in the stem weight and an action of promoting flowering were observed in the treated plot of 0.01 mM in comparison with the untreated plot. This action was observed in the treated plot until the concentration of D-allose was 1 mM, showing the highest value in the treated plot of 0.01 mM although the values of the activity varied. On the contrary, in the treated plot of 5 mM, some growth inhibition was observed.

On the other hand, when germinated seedlings of rice at day 5 after sowing was treated with a solution obtained by dissolving D-psicose in a liquid fertilizer (Kimura B solution) at different concentrations (0.005 to 0.5 mM) and raised by hydroponic culture, there was not so much difference between the untreated plot and the treated plot until the concentration of D-psicose was 0.05 mM (>98%). However, 30% of growth inhibition was observed at 0.1 mM, and at 0.5 mM, the seedling length and the root length were inhibited by 43% and 67%, respectively in the hydroponic culture for 10 days. The seedlings in this treated plot of 0.5 mM were transplanted to a soil pot after the 10-day hydroponic culture and were raised for an additional one week without D-psicose, and then the expression pattern of genes related to the defense using the total RNA of the leaves was assayed. As a result, induction of the expression of genes related to rice disease resistance was observed. Further, the growth inhibition observed during the hydroponic culture is a transient action during the treatment with D-psicose, therefore, by raising the plant without the treatment with D-psicose after transplanting it to the soil, it recovered to the size equal to that of the untreated plot in about 3 weeks.

2) Interpretation of These Actions

It was made clear that a rare sugar, which is a monosaccharide, has an action of regulating the growth of a plant. With regard to the mechanism of such an action, it is necessary to further conduct a study in the future, however, as a present possibility, it is presumed that 1) the rare sugar is involved in the regulation of production of a plant hormone, 2) the rare sugar per se has an action as a hormone related to the growth of a plant, 3) the rare sugar has an action of activating or inhibiting a metabolic pathway related to the growth and so on. The action related to the regulation of the growth of a plant of these rare sugars, which are each a monosaccharide, have not been studies at all so far, and the findings at this time are novel ones. In the case of the allose that exhibits the growth promotion, it can be easily presumed that it is a useful action from the viewpoint of an increase in food production. Further, also in the case of D-psicose that exhibits the growth inhibition, although the growth was inhibited in a transient manner by allowing a plant to absorb D-psicose from the roots, a gene related to disease resistance was induced in leaves even at one week after the treatment. Therefore, it was made clear that the resistance gene is induced as a part of systemic acquired resistance (SAR) Further, the growth inhibition during the treatment was discontinued by discontinuing the treatment, and it was also made cleat that the action is not an irreversible action.

3) Method of Utilizing These Actions

What practical application is presumed by applying the actions of regulating the growth of a plant of these rare sugars? Examples of the presumed practical application will be shown below.

Examples of application of allose that promotes the growth

The use as an agent for raising seedlings for healthy seedlings by mixing allose in a liquid fertilizer for raising seedlings. It is presumed that because the seedlings are healthy seedlings, disease resistance is also enhanced.

Injection agent for a plant with poor growth

Development of a "seed in which germination or growth is promoted" by directly coating a seed with allose and distributing it.

Enhancement of an effect of promoting the growth by spraying or mixing allose onto or in an auxiliary material or agent for agriculture (a growth mat, a water retention agent, a spreading agent or the like)

Enhancement of an effect of promoting the growth by mixing allose in a bactericide, an insecticide, a fertilizer or a liquid fertilizer.

Examples of application of D-psicose that inhibits the growth

By mixing D-psicose in a liquid fertilizer for raising seedlings, inhibition of unnecessary root elongation and enhancement of disease resistance by SAR.

An agent for transiently inhibiting the growth of rice in excessively fertilized paddy field and an agent for enhancing disease resistance by SAR (meaningless overgrowth of rice results in falling down of rice plants due to strong wind or typhoon).

An agent for simplifying transportation of plant body by inhibiting the growth transiently (a small size is advantageous for transportation).

It is expected that the action of growth inhibition of D-psicose that induces SAR is mitigated by using it by mixing with allose.

A plant growth regulator due to a rare sugar and an analogous compound and a treatment method using the growth regulator will be described.

It has been made clear that rare sugars, which are each a monosaccharide, have various physiological activities. Effects of these rare sugars on the growth of a plant were examined, and as a result, it was made clear that a certain rare sugar has an action of growth promotion and another rare sugar exhibits an action of growth inhibition. From now on, by examining an effect of a rare sugar that can be produced on a large scale on regulating the growth one by one, diverse activities will be elucidated, and the practical application thereof as a useful growth regulator can be expected.

he present invention relates to a composition of a plant growth regulator containing a rare sugar that has an effect on the growth of a plant, preferably D-psicose and D-allose. Further, the present invention relates to a method of regulating the growth of a plant comprising supplying any of these plant vitalizers or the composition of a plant growth regulator to a plant. The form of the plant growth regulator of the present invention may be any of a liquid, a paste, a water-dispersible powder, a granule, a powder, a tablet and the like.

As a method of supplying the plant growth regulator of the present invention to a plant, various means can be employed. For example, a method in which a powder or a granule is directly applied as a fertilizer, a diluted aqueous solution is sprayed directly onto a plant such as leaves, stems or fruits, or is injected into the soil, and a method in which it is supplied by diluting and mixing in a hydroponic culture medium or a feed water which comes into contact with roots in such as hydroponic culture or rockwool, or it is added to a medium in tissue culture can be exemplified.

Examples of the plant that can be treated with the plant growth regulator of the present invention include as fruit vegetables, cucumber, pumpkin, watermelon, melon, tomato, egg plant, green pepper, strawberry, okura, green bean, broad bean, pea, green soybean, corn and the like; as leafy vegetables, Chinese cabbage, greens to be pickled, qing-geng-cai, cabbage, cauliflower, broccoli, Brussels sprouts, onion, green onion, garlic, shallot, green chive, asparagus, lettuce, Boston lettuce, celery, spinach, crown daisy, parsley, wild chervil, Japanese parsley, udo, Japanese ginger, Japanese butterbur, Japanese basil and the like; as root vegetables, Japanese radish, turnip, burdock, carrot, potato, aroid, sweet potato, yam, ginger, lotus root and the like. Other than these, it can also be used for rice plants, wheat plants, flowering plants fruit trees and the like. To be more specific, *Salsola komarovii, Diospyros kaki, Clarkia amoena, Myosotis scorpioides*, Chinese lantern plant, *Gomphrena globosa, Antirrhium majus, Limonium dumosum, Scabiosa, Craspedia globosa, Impatiens, Agrostemma* (2 varieties), *Viscaria oculata, Platycodon grandiflorus, Viola, Orychophragmus violaceus, Amaranthus mangostanus* L., cauliflower, snow pea, burdock, qing-geng-cai, German chamomile, chive, summer savory, thyme, hyssop, cinnamon basil, sweet basil, oregano, sage, wheat, corn, sorghum, Italian grass, lemon balm, green pea, chrysanthemum, paludosum, Shasta daisy, *Venidium fastuosum*, Swiss Chard, daisy, *Rodgersia podophylla, Callistephus chinensis, Dianthus barbatus* L., *Calendula officinalis, Lunaria annua*, Asparagus Lettuce, adzuki bean, snow pea, *Ipomoea aquatica, Corchorus olitorius*, green pepper, kale to be used for green juice, tomato, *Canarium album, Brassica juncea* var. *integlifolia*, Leaf lettuce, crown daisy, *Vicia sativa* L. var. *normalis Makino*, green onion, Benrina, *Foeniculum vulgare* Mill, chervil, *Eruca vesicaria*, cilantro leaf, dill, water lettuce, sweet marjoram, Musk melon, rice and the like can be exemplified. Further, it can be used not only for cultivation in a field, but also for tissue culture such as production of mericlone plants and for raising seedlings.

As shown in Example 8, plants (28 species) in which a difference among the treated plots was not clear will be listed.

Sweet pea, cockscomb, cineraria, poppy, *Saponaria ocymoides, Mimosa pudica, Ageratum houstonianum, Helichrysum petiolare, Dianthus chinensis*, Lupinus Russell Hybrids, *Gypsophila elegans, Brassica oleracea* var. *acephala, Brassica juncea* Czern. et Coss. var. *rugosa Kitam*, Konkosai, *Allium schoenoprasum* var. *foliosum, Brassica rapa* var. *peruviridis, Lagenaria siceraria* var. *gourda*, Tokyo Bekana, cabbage, Japanese radish, *Brassica rapa hakabura, Brassica rapa* var. chinensis, radish, Chinese cabbage, eggplant, peppermint, lavender, and garden cress Plants which were not germinated or whose germination rate was low will be listed (23 species, note that those classified into another category in the results of a repeated experiment are also included *).

*Phlox drummondii, Patrinia scabiosaefolia Patrinia*, Chinese lantern plant*, petunia*, *Delphinium ajacis, Aquilegia vulgaris* L., Alyssum, Indian spinach, spinach (3 varieties), celery, wild chervil, *Angelica keiskei, Momordica charantia* L., rosemary, peppermint, lavender, garden cress*, Borage, *Vitis ficifolia, Akebia quinata*, and Muscat Alexandria A difference in germination among families of agricultural crops for D-psicose was not clear, however, in many plants in the Brassica family, germination was inhibited by D-psicose. There were also plants in which not only germination itself was inhibited, but also root elongation or growth of seed leaves after germination was inhibited, or formation of pigment (especially, chloroplasts) was inhibited.

Many plants were inhibited by D-psicose, however, there were plants which were not affected, or were affected in a promoting manner in the tested plants. They were *Clarkia amoena, Diospyros kaki* and *Salsola komarovii*, and it is a very interesting phenomenon, and shows a wide range of value of the rare sugar as a plant growth regulator.

An action of inhibiting the growth of a microorganism of a rare sugar will be described.

By a rare sugar, not only the growth of a plant pathogenic bacterium, but also the growth of a harmful microorganism, that is, a saprophytic bacterium having an unfavorable effect on food production processing, medical facilities, living environments, air-conditioning equipment or the like is inhibited.

Therefore, it can be used as a composition of a microorganism growth inhibitor containing a rare sugar having an effect of inhibiting the growth of a microorganism, preferably D-psicose, D-allose, D-altrose or L-galactose even in a field of other than a plant disease, for example, in a field of a processing plant for fresh food such as precut vegetables, a food production plant, a medical facility, a living environment involving dew formation or the like, air-conditioning equipment involving *Legionella* bacteria or the like. The application form thereof may be any of a liquid, a paste, a water-dispersible powder, a granule, a powder, a tablet and the like, and also an aqueous solution thereof can be directly sprayed onto food or the like.

The composition of a microorganism growth inhibitor according to the present invention can be prepared by, for example, replacing a part or all of the sugars contained in a mixture obtained by adding an organic acid (two or more types of citric acid, a citrate, lactic acid, a lactate, acetic acid, an acetate, malic acid, a malate, tartaric acid, a tartrate, gluconic acid, adipic acid and phytic acid) to a buffered ethanol solution, which is a commercially available ethanol/aqueous bactericide and is prepared by dissolving lactic acid or sodium lactate in ethanol/aqueous solution, and blending a sugar (an oligosaccharide, maltose, trehalose, glucose, starch syrup, a stevia sweetener, rutin, pullulan, dextrin or the like) and thiamine lauryl sulfate therein with a rare sugar. In the case where a sugar is present without deteriorating the taste of a vegetable, by the effect of the lauryl sulfate together with the sweetness thereof, it is useful to improve the shelf life of the vegetable, and further, by the synergistic effect of the buffered ethanol solution, the organic acid and the rare sugar, an action of inhibiting the growth of *E. coli*, *Staphylococcus aureus* and *Clostridium botulinum* can be expected.

The composition of a microorganism growth inhibitor according to the present invention can be used not only in processing of vegetables, but also in an environment of food production, and is characterized in that it can be used by changing the dilution ratio depending on the purpose such as sterilization of meat, sterilization of meat product, sterilization of fish meat cake product, sterilization of the production environment or preparation environment for them, machines, apparatuses, hands and fingers, sterilization of bacteria floating in the air, or the like. It exhibits its effect also on disinfection of containers, dinnerware, dining tables, cooking tables, cutting boards, kitchen knives, kitchen cloth, hands, fingers and the like, and cleansing an eating environment. Further, the composition is used by being diluted as an edible washing agent in principle, and for example, even in the case where cabbage is immersed as it is after prewash is carried out for washing away dirt or the like, or in the case where it is immersed after it is cut into pieces, the composition is used after being diluted, and as for the immersing time, in the case of a vegetable cut into pieces, the effect is sufficiently exhibited by immersing it for 3 minutes. Because the present agent is edible, it is not necessary to wash the vegetable with water after it is immersed, and the agent is characterized in that the vegetable can be eaten as such after water is drained off. Further, a vegetable cut into pieces is placed on a strainer or in a vinyl bag and the agent can be sprayed onto the vegetable.

Further, the composition of a microorganism growth inhibitor can be prepared by replacing a part or all of the sugars contained in a mixture obtained by adding the same organic acid to the same buffered ethanol solution, which is a commercially available edible washing agent and blending a sucrose ester, a monoglyceride and a sugar therein with a rare sugar. By the addition of the bactericidal activity of the monoglyceride to the synergistic effect of the buffered ethanol solution, the organic acid and the rare sugar, and further by the washing effect of the sucrose ester and the improvement of removal rate of bitter taste of vegetable by the organic acid, the composition exhibits an effect of removal of such as an agricultural chemical, and has a strong inhibitory effect on aerobic Gram-positive bacteria belonging to such as the genus *Bacillus* or the genus *Micrococcus*, and has an effect of preventing discoloration of vegetable. The composition is used for the purpose of directly spraying it onto food or immersing food in a food production environment, and also is used for killing or eliminating bacteria for cutters, work knives, cutting boards, work tables, hands, fingers and gloves to be used in food processing. In particular, when it is used in an equipment environment in which there is excessive moisture such as sinks, the composition has a characteristic that its bactericidal activity is not lowered even if it is diluted, therefore, it can be used by being arbitrarily diluted depending on the subject of use.

Hereinafter, the present invention will be described in detail with reference to Examples. The present invention is by no means limited by these Examples.

EXAMPLE 1

[Materials and Methods]
Cut leaves of rough lemon were treated by spraying each of 0.5 mM L-psicose, L- & D-tagatose and D-sorbose thereon and were let stand for 2, 4, 6, 12, 24 and 48 hours at 24° C. under the dark condition in a moist chamber. Then, from the treated leaves, total RNA was extracted and the expression of genes of lipoxygenase and chitinase was analyzed by Northern blotting. The assays and analyses were repeated at least 3 times in all the treated plots, and equivalent results were obtained.

[Results and Discussion]
As a result of treating rough lemon by spraying D-psicose, and other than this, L-psicose, L- & D-tagatose or D-sorbose thereon, and analyzing the expression of genes of lipoxygenase and chitinase, which are defense-related genes, by Northern blotting, among the various rare sugars tested, in the case where the treatment was carried out with D-psicose, induction of the expression of lipoxygenase gene could be maintained for the longest time. Also in the plots treated with other rare sugars, induction of the expression of lipoxygenase gene during the early stage could be observed, however, the persistency thereof was low, and the effect was almost lost in 24 hours after the treatment. These results indicate the possibility that D-psicose plays the most effective role as a factor of stress signaling among the rare sugars which had been tested so far (FIG. 2).

In general, it is considered that signal transduction pathways in plants are involved in a wide variety of processes. However, it has been made clear that D-tagatose induces the expression of chitinase gene more strongly than D-psicose, which shows the possibility that a rare sugar can also induce a stress reaction or a signal transduction pathway other than the pathway induced by D-psicose. Chitinase is known as an antibacterial protein that degrades a bacterial cell wall component and it is known that in many plants used for studies, the gene expression is induced after a lapse of a certain period of time after bacterial inoculation. Therefore, it is presumed that the induction is carried out by a signal transduction pathway different from a defense-related gene that responds quickly such as lipoxygenase described above.

By carrying out an assay using more rare sugars in the future, it is expected that a plurality of signal transduction pathways in plants can be artificially induced simultaneously or at different times (FIG. 3).

EXAMPLE 2

Effect of D-psicose on Expression of Gene in *Lotus japonicus*

A pattern of induction of a gene in the case where D-psicose was added to a medium for *Lotus japonicus* was examined by an experiment using a cDNA array.

[Materials and Methods]
*Lotus japonicus* was germinated from a seed and cultivated in an L&B medium (hydroponic culture medium). When the seed was germinated, *Mesorhizobium loti* was also inoculated. This condition was applied to both a control plot and a plot of D-psicose addition. With regard to the array, a microarray on which 14,000 clones were immobilized by using a *Lotus japonicus* cDNA array was used. After test plants were germinated, they were cultivated with an L&B medium supplemented with D-psicose or without addition for 1 week in a growth cabinet (22° C., 30,000 Lux). After total RNA was extracted from the plant body, it was labeled with $^{33}$P in the process where it was converted to cDNA, and then hybridization was carried out. Reading was carried out using STORM 850 and analysis was carried out with Array Vision.

[Results and Discussion]
In *Lotus japonicus* to which 5 mM D-psicose was given, a gene group that responds to a variety of pathogenic bacteria and environmental stresses such as genes of chitinase and PR10 protein and genes that respond to a salt stress and a dehydration stress were activated in the first one week (Table 8). This effect was not observed in the case of 5 mM D-fructose. When the concentration of D-psicose in the medium was about 0.1 mM, an increase or a decrease in the expression of a gene group regulated by plant hormones such as auxin was observed rather than the stress response gene group. These effects of the addition of D-psicose were several times or more larger than those of D-fructose. Therefore, it was predicted that when D-psicose is given to roots at a concentration of about 0.1 mM, it has various effects on the growth of the plant.

TABLE 1

| | Expression ratio (D-psicose/water) |
|---|---|
| Stress/hormone response gene in which an increase in the expression is detected (psicose: 5 mM) | |
| class I chitinase | 13.2 |
| PR-10-1 protein | 5.5 |
| cytochrome P450 monooxygenase | 8.1 |
| chalcone synthase | 5.4 |

TABLE 1-continued

| | Expression ratio (D-psicose/water) |
|---|---|
| ACC oxidase | 5.1 |
| auxin response factor like protein | 5.6 |
| PDR5-like ABC transporter | 10.8 |
| Stress/hormone response gene in which an increase in the expression is detected (psicose: 0.1 mM) | |
| auxin response factor 6 (ARF6) | 2.5 |
| glycine-rich RNA-binding, abscisic acid-inducible protein | 2.5 |
| metal stress-regulated protein SR7 | 2.4 |
| pathogen-inducible alpha-dioxygenase | 2.4 |
| auxin-binding protein T85 precursor (ABP) | 2.4 |
| turgor-responsive protein 26G | 2.3 |
| chitinase | 2.2 |
| putative WD-40 repeat protein | 2.2 |
| chitinase (EC 3.2.1.14) class II | 2.2 |

EXAMPLE 3

[Materials and Methods]

Seedlings of a strawberry plant (variety: "smile ruby") obtained by meristem culture under sterile conditions were used in an experiment.

As for the strawberry, by using ½ strength MS medium supplemented with 0.1% (w/v) D-psicose or D-glucose, the seedling plants were aseptically transplanted on Oct. 14, 2003, and then, cultivation was carried out in a culture chamber at 25° C. and 5,000 Lux (12-hour day length). Then, on Jan. 20, 2004, a survey was carried out with regard to the growth conditions of aerial part and underground part, the number of lateral buds and the like. The results are shown in Table 2.

[Results and Discussion]

As a result of adding 0.1% (w/v) D-psicose to the medium for tissue culture of the strawberry "smile ruby" and examining the effects on the growth thereof and the like, in the plot of D-psicose addition, the values exceeded in all the survey items except for the root length compared with those of the plot without addition which was a control plot. Among these, an increase in the plant length and the aerial part weight was also observed in the plot of D-glucose addition, however, the values of the plot of D-psicose addition exceeded in the underground part weight, the leaf area and the number of lateral buds compared with those of the plot of D-glucose addition. From this result, by adding D-psicose to the medium, the growth and the lateral bud formation were promoted. Many of the primary seedlings to be used for strawberry cultivation at present are virus-free tissue-cultured seedlings obtained by tissue culture. Therefore, it was considered that there is a possibility that the clarification of the effect of promoting the growth of strawberry seedlings by D-psicose leads to reduction of cultivation period or improvement of cultivation efficiency.

Further, as for the strawberry, when the concentration of D-psicose or D-allose added to the medium was increased, the growth thereof was delayed. From this result, it was made clear that D-psicose inhibits the growth at a high concentration, while it has an action of promoting the growth or differentiation at a low concentration. It was made clear that with the use this action, it is possible to regulate the growth of a plant according to the purpose by changing the concentration or amount of a rare sugar.

TABLE 2

| Survey items | Without addition | 0.1% D-glucose | 0.1% D-psicose |
|---|---|---|---|
| Plant length (cm) | 3.0 | 4.3 | 4.5 |
| Aerial part weight (g) | 1.8 | 3.0 | 3.1 |
| Leaf area (cm) | 1.6 | 2.2 | 3.7 |
| Root length (cm) | 8.7 | 8.7 | 7.2 |
| Underground part weight (g) | 0.5 | 1.2 | 1.9 |
| Number of lateral buds | 0.6 | 1.0 | 1.3 |

(Note)
The numerical values represent the averages of the five plants.

EXAMPLE 4

[Materials and Methods]

Seedling plants of Bletilla striata obtained by sterile sowing were used in an experiment.

As for the Bletilla striata, by using ½ strength MS medium supplemented with D-psicose, D-allose, D-glucose or D-fructose at a concentration of from 0.005% to 0.05% (w/v), the seedling plants were aseptically transplanted on Feb. 27, 2003, and then, cultivation was carried out under the same conditions as those of the strawberry in Example 3. Then, on Jun. 30, 2003, a survey was carried out with regard to the growth conditions of aerial part and underground part, the number of buds, the ratio of bulb formation, the bulb size and the like. The results are shown in Table 3.

[Results and Discussion]

To a medium for tissue culture of Bletilia striata, D-psicose and D-allose were added at a concentration of from 0.005% (w/v) to 0.05% (w/v), and the effects on the growth, bulb formation and the like were examined. As a result, although no significant difference was observed in terms of the number of buds and the number of leaves compared with the plot without addition which was a control plot, the plot of D-glucose addition and plot of D-fructose addition. However, a tendency was observed that the plant length, the maximum root length, the aerial part weight, the underground part weight were increased by the addition of D-psicose at a low concentration (0.005% (w/v) and 0.02% (w/v)). From this result, it was made clear that D-psicose exhibits an effect of promoting the growth of Bletilla striata. Further, although a tendency was observed that the ratio of bulb formation was increased in the whole of the plots of sugar addition, it was significantly increased by adding D-allose. At present, as for many of the orchids introduced to Japan from the West such as Phalaenopsis orchid and Cymbidium, mericlone plants obtained by tissue culture are used, which has played an important role in the reduction of the production cost and the popularization thereof. It was considered that there is a possibility that the clarification of the effect of promoting the growth of Bletilla striata seedlings or the effect of improving the ratio of bulb formation by D-psicose or D-allose leads to reduction of cultivation period or improvement of cultivation efficiency in the same manner as the strawberry.

Further, also for Bletilla striata, when the concentration of D-psicose or D-allose added to the medium was increased, the growth thereof was delayed in the same manner as the strawberry. From this result, it was made clear that these rare sugars inhibit the growth at a high concentration, while they have an action of promoting the growth or differentiation at a low concentration. It was made clear that with the use this action, it is possible to regulate the growth of a plant according to the purpose by changing the concentration or amount of a rare sugar.

TABLE 3

| Type of sugar | Sugar concentration (%) | Maximum plant length (cm) | Aerial part weight (g) | Maximum root length (cm) | Underground part weight (g) |
|---|---|---|---|---|---|
| non | non | 4.5 | 0.11 | 3.7 | 0.04 |
| D-glucose | 0.005 | 7.3 | 0.15 | 4.9 | 0.13 |
|  | 0.02 | 7.2 | 0.20 | 5.1 | 0.18 |
|  | 0.05 | 6.5 | 0.18 | 6.1 | 0.14 |
| D-fructose | 0.005 | 6.5 | 0.16 | 4.6 | 0.15 |
|  | 0.02 | 6.6 | 0.19 | 5.1 | 0.14 |
|  | 0.05 | 7.3 | 0.19 | 4.1 | 0.10 |
| D-psicose | 0.005 | 9.3 | 0.24 | 4.4 | 0.26 |
|  | 0.02 | 9.9 | 0.28 | 4.8 | 0.22 |
|  | 0.05 | 7.3 | 0.20 | 5.3 | 0.13 |
| D-allose | 0.005 | 7.6 | 0.19 | 4.2 | 0.10 |
|  | 0.02 | 7.5 | 0.19 | 4.1 | 0.12 |
|  | 0.05 | 7.7 | 0.25 | 4.2 | 0.12 |

| Type of sugar | Sugar concentration (%) | Number of buds | Number of leaves | Ratio of bulb formation (%) | Bulb size (mm) |
|---|---|---|---|---|---|
| non | non | 3.7 | 4.6 | 41 | 4.2 |
| D-glucose | 0.005 | 3.7 | 4.1 | 37 | 5.1 |
|  | 0.02 | 3.4 | 3.9 | 59 | 5.7 |
|  | 0.05 | 3.4 | 4.0 | 45 | 5.2 |
| D-fructose | 0.005 | 3.7 | 3.5 | 44 | 5.2 |
|  | 0.02 | 3.3 | 4.6 | 67 | 4.5 |
|  | 0.05 | 3.3 | 4.0 | 69 | 4.7 |
| D-psicose | 0.005 | 4.1 | 3.9 | 45 | 6.2 |
|  | 0.02 | 3.3 | 3.9 | 65 | 5.6 |
|  | 0.05 | 4.0 | 3.9 | 67 | 5.1 |
| D-allose | 0.005 | 3.4 | 4.2 | 84 | 4.5 |
|  | 0.02 | 3.6 | 3.9 | 85 | 4.2 |
|  | 0.05 | 2.7 | 4.3 | 85 | 4.9 |

(Note)
The numerical values represent the averages of the nine plants.

EXAMPLE 5

[Materials and Methods]

A strawberry plant (variety: "smile ruby") was used in an experiment. The strawberry plants were planted in pots and from Feb. 13, 2004, while the cultivation was carried out in a glass house, water or a 0.5% (w/v) sugar solution was sprayed onto the whole plant on a three times weekly basis. As for the types of sugars, D-glucose and D-psicose were used and two pots were cultivated for each test plot. While the cultivation was continued, the number of fruits, the weight of fruits, the sugar content of fruits were measured with regard to the fruits that could be harvested by Mar. 25, 2004. The results are shown in FIG. 4.

[Results and Discussion]

The number of fruits that could be harvested during the cultivation period was increased from 25 to 38 by spraying D-psicose. Further, the average weight of fruits was increased from 13.5 g to 16.6 g by spraying D-psicose. As a result, the total weight of fruits that could be harvested during the cultivation period was increased from 337.8 g to 630.3 g by spraying D-psicose. From this result, it was made clear that by the foliar spraying of D-psicose onto the strawberry, it is possible to increase the number of fruits and the weight of fruits, therefore, it is effective in increasing the yield.

EXAMPLE 6

[Materials and Methods]

After seeds of a rice plant (variety: "Hinohikari") were put in a nylon net and subjected to sterilization and a germination induction treatment in a growth chamber at 30° C. for 2 days while they were soaked in 0.1% (w/v) Benlate (Hokko Chemical Industry Co., Ltd.) in accordance with a common method, they were sown in a nursery tray filled with "Kumiai Ryujou Baido SD" (Kureha Chemical Industry Co., Ltd.) and raised in a phytotron (day temperature: 25° C. and night temperature: 18° C.) for about 2 weeks. Then, Wagner pots with a size of 1/5,000a were filled with "Kumiai Ryujou Baido SD" (Kureha Chemical Industry Co., Ltd.) and the raised rice seedlings were transplanted for permanent planting to the pots and the cultivation was started on Jul. 2, 2003 in the open air under the condition that the soil was covered with water in the pots. From Jul. 16, 2003, when the seedlings were confirmed to take root, water, a 0.02% (w/v) sugar solution, a 0.1% (w/v) sugar solution or a 0.5% (w/v) sugar solution was sprayed onto the whole plant on a three times weekly basis. As for the types of sugars, D-glucose, D-fructose and D-psicose were used and three pots were cultivated for each test plot. The cultivation was continued in such a manner that the water in pots was not dried up and after 5 g of Magamp K medium (HYPONeX JAPAN CORP., Ltd.) per pot was added as additional fertilization on Aug. 29, 2003, and the harvest and survey were carried out on Sep. 22, 2003. The survey items were plant length, number of tillers, leaf weight, husk weight, underground part weight and the like. The results are shown in Table 4.

[Results and Discussion]

Compared with the plot sprayed with water that was a control plot, no significant effect was exhibited in the plot sprayed with D-glucose and the plot sprayed with D-fructose, however the plant length, the leaf weight and the husk weight were deceased as the concentration of D-psicose was increased in the plot sprayed with D-psicose and an effect on inhibiting the growth and the yield was exhibited. Contrary to this, the number of tillers was increased. From the above result, it was made clear that D-psicose has effects on inhibiting the growth and increasing the number of tillers in rice.

TABLE 4

| Type of sugar | Sugar concentration (%) | Plant length (cm) | Number of tillers | Dry leaf weight (g) | Dry husk weight (g) |
|---|---|---|---|---|---|
| non | non | 80.7 | 34.0 | 41.8 | 14.9 |
| D-glucose | 0.02 | 74.0 | 29.3 | 34.0 | 17.2 |
| | 0.10 | 75.5 | 30.0 | 35.5 | 17.6 |
| | 0.50 | 74.8 | 31.3 | 37.3 | 17.9 |
| D-fructose | 0.02 | 85.7 | 29.3 | 43.3 | 16.8 |
| | 0.10 | 84.3 | 29.3 | 41.0 | 16.1 |
| | 0.50 | 85.7 | 27.0 | 36.4 | 17.2 |
| D-psicose | 0.02 | 73.2 | 33.7 | 36.3 | 16.8 |
| | 0.10 | 76.3 | 33.5 | 31.8 | 14.7 |
| | 0.50 | 71.3 | 50.0 | 27.9 | 10.2 |

The numerical values represent the averages at the three plants.

EXAMPLE 7

[Materials and Methods]

*Brassica rapa* var. *amplexicaulis* is a vegetable in the Brassica family, and flower buds are harvested and used. As the same species of vegetables, broccoli, cauliflower and the like are exemplified, which are important horticultural crops. As for such a vegetable, development of flower buds has a large effect on the crop yield. Therefore, during the house cultivation of *Brassica rapa* var. *amplexicaulis* (variety: "Haru Ichiban"), foliar spraying of a sugar solution at a concentration of 0.5% (w/v) was carried out and effects on the growth and the development of flower buds were examined. The seeds of *Brassica rapa* var. *amplexicaulis* were sown in a 128-cell tray on Oct. 23, 2003 and raised for about 20 days. Then, the raised seedlings were transplanted for permanent planting with a planting distance of 40 cm on two rows with an inter row space of 50 cm in separate beds filled with soil for cultivation "Hana to Yasai no Tsuchi (garden soil for flowers and vegetables)" (Kurokawa Shubyo En) on Nov. 12, 2003. The cultivation was carried out by a simple fertigation system, and irrigation was carried out for 1 hour on a daily basis with a 2,000-fold dilution of Hyponex through an irrigation tube. The cultivation was carried out in a vinyl house without heating with side windows open. From Dec. 18, 2003, water or a 0.5% (w/v) sugar solution was sprayed onto the whole plant on a three times weekly basis. As for the types of sugars, D-glucose, D-fructose and D-psicose were used and five plants were cultivated for each test plot. On Feb. 23, 2004, three plants of medium size were harvested and a survey was carried out. The survey items were plant length, stem diameter, number of lateral buds, terminal bud weight, total weight of lateral buds and the like. The results are shown in Table 5.

[Results and Discussion]

As a result of the cultivation test of *Brassica rapa* var. *amplexicaulis*, compared with the plot sprayed with water that was a control plot, there was a tendency that the plant length was increased on the whole in the plot sprayed with a sugar. In the plot sprayed with D-fructose, there was a tendency that the number of lateral buds was increased, however, in the plot sprayed with D-psicose and the plot sprayed with L-galactose, the plant length, the stem diameter and the number of lateral buds were further increased, therefore, it was considered that they have an effect of promoting the growth and an effect of promoting the differentiation into flower buds. Further, as for the total weight of lateral buds, even in the plot sprayed with D-psicose and the plot sprayed with L-galactose, no difference was observed compared with the other test plots, however, it is considered that the reason is that the survey was carried out at an earlier stage than the ordinary harvesting stage due to the surveying reasons, therefore, the development of lateral buds were not sufficient. Accordingly, judging from the fact that the growth was strong and the number of lateral buds was large, it is expected that in the plot sprayed with D-psicose and the plot sprayed with L-galactose, by continuing the cultivation, the final total weight of lateral buds will exceed that of other test plots. From the above result, it was made clear that the growth and the development of flower buds are promoted by foliar spraying of D-psicose or L-galactose during the cultivation of *Brassica rapa* var. *amplexicaulis*.

TABLE 5

| Test plot | Plant length (cm) | Stem diameter (mm) | Number of lateral buds | Terminal bud weight (g) | Total weight of lateral buds (g) |
|---|---|---|---|---|---|
| Control plot (water) | 49.3 | 22.8 | 32.3 | 3.0 | 235.3 |
| 0.5% D-glucose | 56.3 | 20.6 | 32.0 | 5.7 | 198.1 |
| 0.5% D-fructose | 55.8 | 19.9 | 41.3 | 7.4 | 231.1 |
| 0.5% D-psicose | 61.2 | 26.9 | 43.0 | 8.8 | 225.0 |
| 0.5% D-allose | 60.7 | 23.6 | 38.0 | 7.9 | 222.5 |
| 0.5% L-galactose | 52.7 | 21.7 | 48.3 | 9.6 | 250.6 |

(Note)
The numerical values represent the averages of the three plants.

EXAMPLE 8

When a dormant branch of a grape was treated with D-psicose, an interesting result was obtained.

[Materials and Methods]

1. Effect of D-psicose on dormant branch of wild grape *Vitis kiusiana Momiyama*

Matured branches of a Japanese wild grape *Vitis kiusiana Momiyama*, in which rooting of cuttings is difficult (Mochioka et al., Plant Tissue Culture 13: 139-145, 1996; Journal of ASEV JAPAN 13: 2-8, 2002) and dormancy of buds is deep (Mochioka et al., Journal of Japanese Society for Horticultural Science, 65: 49-54, 1996) were collected in January during the dormant stage, and stored under refrigeration in such a manner that they were not dried. On March 11, they were prepared to have one bud. After each cutting base was immersed in a 3% aqueous solution of D-psicose (supplemented with a spreading agent, Approach BI at 0.2%) for 24 hours, on the following day March 12, it was planted in a Vermiculite bed and placed in a temperature-controlled chamber at 25° C. and 16-hour day length, and the bud flush rate with time was measured. The timing of bud flush was determined to be a time when bud scale leaves fall off and about 50% of the tomentum that protects the bud appears. In a control plot, the cutting base was immersed in distilled water supplemented with 0.2% Approach BI for 24 hours, and then, subjected to the same treatment as described above.

In the survey of the bud flush rate, 9 cuttings were used for each plot and the procedure was repeated three times and an average was obtained.

2. Effect of D-psicose on dormant branch of cultivated variety of "*Vitis vinifela* L."

Matured branches of "*V. vinifera* L." grown outdoors were collected on December 25 during the dormant stage and were prepared to have one bud, and then, each cutting base was immersed in a 0.01, 0.1 or 1% aqueous solution of D-psicose for 24 hours. On the following day December 26, the same procedure as in 1 was carried out. In a control plot, distilled water was used, and to the liquid for treatment, Approach BI was not added. The judgment of bud flush was carried out in accordance with the method in 1. The measurement of bud flush was carried out on about a weekly basis.

In the survey of the bud flush rate, 9 cuttings were used for each plot and the procedure was repeated twice and an average was obtained.

[Results and Discussion]

1. Effect of D-psicose on dormant branch of wild grape *Vitis kiusiana Momiyama*

A change of the bud flush rate of *Vitis kiusiana Momlyama* is shown in FIG. 5. In the control plot, the bud flush occurred in mid-April, however, in the plot treated with D-psicose, the bud flush occurred from late March. Further, throughout the whole period, in the plot treated with D-psicose, a higher bud flush rate was exhibited than in the control plot.

2. Effect of D-psicose on dormant branch of cultivated variety of "*Vitis vinifera* L."

A change of the bud flush rate of "*Vitis vinifera* L." is shown in FIG. 6. Until early February, the bud flush rate was lower in all the plots treated with D-psicose than in the control plot, however, after the mid-February, in the plot treated with 1% psicose, the bud flush rate changed while it showed the highest value. Further, in the plot treated with 0.01% D-psicose, the bud flush rate showed a similar pattern to that of the control plot, however, in the plot treated with 0.1% D-psicose, the bud flush rate changed while it showed the lowest value throughout the whole period.

When the same treatment as in 2 was carried out by using green branches of grapes in summer, in the plot treated with 1% D-psicose, the branches were withered and dead (data omitted). From this result, it is presumed that D-psicose at a concentration not lower than 1% imposes an extremely strong stress on the branches of grapes. It is considered that as for a substance for breaking of dormancy of buds of grapes, a cyan compound produced as a byproduct in the ethylene production pathway is greatly involved (Tobu et al. Journal of Japanese Society for Horticultural Science, 67: 897-901, 1998a; Journal of Japanese Society for Horticultural Science, 67: 902-906, 1998b). Therefore, it is presumed that by the treatment with D-psicose at a high concentration, production of ethylene proceeds, and a cyan compound is produced, whereby dormancy is broken.

Further, a rare sugar also has a radical scavenging ability for such as active oxygen, therefore, it was considered that the treatment with D-psicose at an appropriate concentration inhibited the ethylene production and the substance for breaking of dormancy is not produced, and as a result, the bud flush rate was decreased. Fuchigami Nee (Hort Science 22: 836-845, 1987) presumed that glutathione which takes responsibility for oxidation and reduction reactions in vivo may play an important role in the regulation of dormancy. Glutathione is an organic compound with a low molecular weight that is widely distributed in vivo in plants and animals, works as a kind of coenzyme and is considered to act on as an antioxidant that protects a thiol group (SH group) of an enzyme or a protein (Rennenberg, Phytochemistry 21: 2771-2781, 1982). Fuchigami Nee reported (1987) that when dormant buds of a pear plant "Super Tret" was treated by using cyanamide which is a cyan compound having an effect on breaking of dormancy of buds (Tobu et al., 1998b), a carbon atom of cyanamide was confirmed to be bound to an SH group of a reduced form of glutathione (GSH) in the bud without resort to the activity of an enzyme, and when these are bound to each other, the effect of cyanamide on breaking of dormancy was lost. Further, it has been reported that in the case where cyanamide reacts with an oxidized form of glutathione (GSSG) in vivo, GSSG is converted into GSH, and as a result, purification of a polyamine, ethylene, arginine and the like is promoted (Wang et al., 1985). Further, a stress (freezing, drying or the like) at a level not more than lethal dose immediately promotes production of GSH due to synthesis or reduction of GSSG (Fuchigami Nee, 1987).

From these facts, it is presumed that a rare sugar has some kind of influence also on glutathione.

In general, it is known that the phenomenon of dormancy of buds of cultivated grapes begins at around September when maturation of branches proceeds, and the primary dormancy is deepest between October and early November, and thereafter, the dormancy is gradually broken and breaking of dormancy is almost completed by around late January (Horiuchi, dissertation submitted to Osaka Prefecture University, 1977; Okamoto, pp. 57-62, Nogyo Gijutsu Taikei, Kajuhen 2, Rural Culture Association Tokyo, 1981). At this time, because branches in the secondary dormant stage after finishing the primary dormancy were used, no clear difference among the treated plots was observed, however, it is expected that by D-psicose treatment was carried out using branches during the stage of the deepest primary dormant just before leaves fall off, the difference will be clear.

At present, among substances to be used as an agent for breaking of dormancy, there are nitrolime and cyanamide, however, these cyan compounds have an action of inhibiting respiration. Therefore, when the timing of use is late or the temperature during use is high, a chemical damage such as withering of buds occurs or the effect on breaking of dormancy is unstable in some cases. In addition, symptoms of acute alcoholic poisoning are caused in some cases by inhibiting aldehyde dehydrogenase, suppressing ethanol metabolism in the liver and accumulating acetaldehyde. Therefore, when they are used, it is necessary to pay attention on the health aspect in some cases. A rare sugar does not have any problems in terms of the above point, therefore, there is a possibility that the rare sugar becomes an agricultural chemical that is not harmful to the environment and human body.

EXAMPLE 9

Effect of Rare Sugar on Seed Germination I

[Purpose]

Seeds are in a state of primary or secondary dormancy until they are sown, however, when a condition suitable for germination is provided, seeds immediately start to germinate except for hard seeds. In general, because seeds have nutrients necessary for germination such as alubumen and a seed leaf, an effect when a sugar is exogenously provided is hardly known except for a study of sterile germination of an orchid which is an exalbuminous seed.

In this Example, with regard to an effect of a rare sugar, D-psicose, on germination of plant seeds was examined compared with the case of D-fructose, which is a common sugar, and further, comparison with other some rare sugars was also carried out.

[Materials and Methods]

Experiment 1 (Effect of Continuous Treatment)

Seeds of vegetables (11 families and 51 species or varieties); ornamental plants (19 families and 47 species or varieties); halves (4 families and 14 species or varieties); fruit trees (3 families and 3 species or varieties); grains (1 family and 3 species or varieties); and feed crops (1 family and 3 species or varieties) were continuously treated with any of 4 types of solutions of deionized water (control), 1% D-fructose, 1% D-psicose and 0.5% D-fructose+0.5% D-psicose and germinated under the condition of 25° C., 35 µmol·m$^{-2}$·s$^{-1}$, and 16-hour lighting or 16-hour dark. As for the number of seeds, 50 seeds were used for each solution basically, and when the number of seeds was small, the seeds were distributed in such a manner that the number of seeds for each solution became equal. The seeds were sown in a dish with a diameter of 9 cm having a filter paper placed therein or when the seeds were large, they were sown in a styrol container with a diameter of 10 cm and a height of 45 mm. Then, 10 ml or 50 ml of any of the solutions was poured therein, and deionized water was suitably added depending on the transpiration.

Experiment 2 (Effect of Short-Time Treatment)

In order to clarify an effect of a short-time treatment, 50 seeds of Salsola komarovii, tomato (Home Momotaro) and sunny lettuce (Red Wave), and 20 seeds of morning glory (Tairin Zaki Kongo) were immersed in any of deionized water, 1% D-psicose, 1% D-allose and 1% L-galactose for 24 hours (25° C., dark), respectively, then, they were lightly washed with deionized water. Then, the seeds were sown in a dish with a diameter of 9 cm having a filter paper placed therein, and germinated under the same condition by poring 5 to 10 ml of deionized water therein. Further, for the comparison, a continuous treatment with 1% D-psicose was carried out in accordance with the same procedure.

[Results and Discussion]

(Effect of Continuous Treatment)

A mode in which germination occurred varied depending on the species, and there were various modes, for example, the seed coat was ruptured and a root elongated (Pea family, etc.); a seed leaf emerged concurrently with germination (Brassica family, etc.); a root emerged from the germination pore (Chenopodiaceae family, Ebenaceae family, etc.); and the like, and there was also a mode in which a seed absorbed water thereby to cover the surface of the seed with a gelled substance and a root emerged therein (*Chrysanthemum multicaule*, etc.).

The number of days required for initiation of germination varied from within one day (lettuce, etc.) to seven days or more (*Diospyros kaki*), however, germination itself was roughly classified as follows.

(i) Germination was Not Affected or was Promoted Slightly by D-psicose (3 species)

*Salsola komarovii, Diospyros kaki* (Only germination was promoted. Elongation of roots was inhibited. See FIG. 7) and *Clarkia amoena*

(ii) Germination was Significantly Inhibited by D-Psicose (2 Species).

*Myosotis scorpioides* and Chinese lantern plant (iii) Inhibition of Germination by D-Psicose was Mitigated by D-Fructose (32 species).

*Gomphrena globosa, Antirrhium majus, Limonium dumosum, Scabiosa, Craspedia globosa, Globosa, Impatiens, Agrostemma* (2 varieties), *Viscaria oculata, Platycodon grandiflorus*, Viola, *Orychophragmus violaceus, Amaranthus mangostanus* L., cauliflower, snow pea, burdock, qing-gengcai, German chamomile, chive, summer savory, thyme, hyssop, cinnamon basil, sweet basil, oregano, sage, wheat, corn, sorghum, Italian grass and local varieties of vegetables (2 varieties)

(iv) Germination was Promoted by D-Fructose (2 species).

Lemon Balm and Green Pea (v) Germination was Inhibited by Both D-Psicose and D-Fructose (41 species).

Chrysanthemum, paludosum, Shasta daisy, *Venidium fastuosum*, Swiss Chard, daisy, *Rodgersia podophylla, Callistephus chinensis, Dianthus barbatus* L., *Calendula officinalis, Lunaria annua*, Asparagus Lettuce, adzuki bean, snow pea, *Ipomoea aquatica, Corchorus olitorius*, green pepper, kale to be used for green juice, tomato, *Canarium album*, green chive, *Brassica juncea* var. *integlifolia*, Leaf lettuce, crown daisy, parsley, broccoli, carrot, *Vicia sativa* L. var. *normalis Makino*, turnip, onion, green onion, parsley, Benrina, *Foeniculum vulgare* Mill, chervil, *Eruca vesicaria*, cilantro leaf, dill, water lettuce, sweet marjoram, Musk melon and rice (vi) A difference among the treated plots was not clear (28 species).

Sweet pea, cockscomb, cineraria, poppy, *Saponaria ocymoides, Mimosa pudica, Ageratum houstonianum, Helichrysum petiolare, Dianthus chinensis*, Lupinus Russell Hybrids, *Gypsophila elegans, Brassica oleracea* var. *acephala, Brassica juncea* Czern. et Coss. var. *rugosa Kitam, Konkosai, Allium schoenoprasum* var. *foliosum, Brassica rapa* var. *peruviridis, Lagenaria siceraria* var. *gourda*, Tokyo Bekana, cabbage, Japanese radish, *Brassica rapa hakabura, Brassica rapa* var. *chinensis*, radish, Chinese cabbage, eggplant, peppermint, lavender and garden cress (vii) Germination Did not Occur or the Germination Rate was Low (23 Species, Note that Those Classified into Another Category in the Results of a Repeated Experiment are also Included *)

*Phlox drummondii, Patrinia scabiosaefolia Patrinia*, Chinese lantern plant*, petunia*, *Delphinium ajacis, Aquilegia vulgaris* L., Alyssum, Indian spinach, spinach (3 varieties), celery, wild chervil, *Angelica keiskei, Momordica charantia* L., rosemary, peppermint, lavender, garden cress*, Borage, *Vitis ficifolia, Akebia quinata* and Muscat Alexandria A difference in germination among families of the agricultural crops for D-psicose was not clear, however, germination of many plants in the Brassica family was inhibited by D-psicose. There were also plants in which not only germination itself was inhibited, but also root elongation or growth of seed leaves after germination was inhibited, or formation of pigment (especially, chloroplasts) was inhibited.

Many plants were inhibited by D-psicose, however, there were plants which were not affected, or were affected in a promoting manner in the tested plants. They were *Clarkia amoena, Diospyros kaki* and *Salsola komarovii*, and it is a very interesting phenomenon, and shows a wide range of value of the rare sugar as a plant growth regulator.

Experiment 2 (Effect of Short-Time Treatment)

As for tomato, sunny salad and morning glory, germination was inhibited by the continuous treatment with 1% D-psicose, however, a clear difference was not observed in other treated plots. On the other hand, as for *Salsola komarovii*, germination was promoted by the continuous treatment with 1% D-psicose in a similar manner, however, as time passed, DW and 1% D-psicose were catching up (28%), and in the end, 1% L-galactose provided the highest germination rate (34%), while with the use of 1% D-allose, germination rate was inhibited, resulting in 16% (see FIG. 8).

As described above, through the two experiments, it was determined that a rare sugar acts on germination of plant seeds in an inhibitory manner as a whole. However, such an effect is diverse, and in some types of plants, a promoting effect was observed. There are an extremely large number of species of flowering plants that produce seeds and also there are many types of rare sugars, therefore, there is a possibility that an unexpected result can be obtained.

EXAMPLE 10

Effect of Rare Sugar on Seed Germination II

Among a variety of ketoses, D-psicose has the highest elicitor activity (activity of inducing systemic acquired resistance). This indicates that when a rare sugar is used as an inducer of systemic acquired resistance, D-psicose exhibits the strongest action.

[Contents of Implementation]

An effect of 8 types of ketoses on germination of *Arabidopsis thaliana* LER series which was an experimental plant was examined.

Two sheets of filter paper were placed in a dish with a diameter of 3.5 cm, and 30 seeds of *Arabidopsis thaliana* Landsberg erecta (LER) were sown per dish, and 0.5 mL of a treatment liquid was poured therein. Then, the dishes were placed in an environment control chamber under the condition of a constant temperature of 25° C. and 24-hour day length (fluorescent lamp, 70 µmol/m$^2$/s). After the sowing, a survey was carried out with regard to the number of seeds that germinated at 24-hour interval. As the treatment liquid, 100 mM, 10 mM and 1 mM aqueous solutions of any of D-fructose, D-psicose, D-tagatose, D-sorbose, L-fructose, L-psicose, L-tagatose and L-sorbose, and distilled water were used. The procedure was repeated three times for the respective treatment liquids.

[Results]

The results are shown in FIG. 9. It was only D-psicose that clearly inhibited germination at 100 mM. With the use of other sugars including L-psicose, inhibition of germination was not clearly observed. In general, it is known that when the concentration of sugar is high, inhibition of water absorption occurs because of the osmotic pressure thereby to inhibit seed germination. However, when the condition of seeds was observed, even by the treatment with 100 mM D-psicose, the seeds swelled by absorbing water and many ruptured seeds were confirmed. Accordingly, it is presumed that after seeds absorb water, germination is inhibited.

EXAMPLE 11

Effect of D-Psicose on Growth of Cherry Tomato

[Purpose]

An effect of a treatment with D-psicose on growth of cherry tomato was examined.

[Materials, Methods, Results and Discussion]

On Jun. 10, 2003, a cherry tomato plant "mini carol" was transplanted for permanent planting to a hydroponic apparatus, and from 7 days after the permanent planting, 4 treated plots (0%, 0.001%, 0.01% and 0.03%) were prepared by adding D-psicose to a nutrient culture solution. A survey was carried out with regard to the growth at 2 weeks after the treatment (July 22). As a result, the stem length was slightly longer in the plots of 0.001% and 0.01%, and was slightly shorter in the plot of 0.03% compared with the control plot. The stem diameter was slightly larger in the plot of 0.01%, and was slightly smaller in the plot of 0.03% compared with the control plot. The number of leaves was slightly larger in the plot of 0.001%, and was slightly smaller in the plot of 0.03% compared with the control plot. The maximum root length was slightly longer in the plot of 0.001%, and was slightly shorter in the plots of 0.01% and 0.03% compared with the control plot. The fresh weight was larger in the plot of 0.001%, and was smaller in the plot of 0.03% compared with the control plot. When the fresh weight was seen according to the parts, roots and leaves were larger in the plot of 0.001%. The number of flower clusters which were developed to a degree that one could recognize by the naked eye was 2.0 in the control plot, and was slightly larger in the plot of 0.001%, and was slightly smaller in the plot of 0.03% compared with the control plot.

Subsequently, a cherry tomato plant "mini carol" was transplanted for permanent planting to a hydroponic apparatus, and a total of 7 treated plots in which a plot without addition (control plot) was added to 6 treated plots with the use of a nutrient solution supplemented with 0.05 mM or 0.5 mM D-psicose, D-fructose or mannitol were prepared. A survey was carried out with regard to the growth at 10 days after the permanent planting. As a result, the stem length was the longest in the case of 0.5 mM D-fructose, and was the second longest in the treated plot of 0.05 mM D-psicose or the like, and was the shortest in the case of 0.5 mM D-psicose. The stem diameter was the smallest in the case of 0.5 mM D-psicose. The number of leaves was the smallest in the case of 0.5 mM D-psicose and 0.5 mM mannitol. The root length was the smallest in the case of 0.5 mM psicose. The fresh and dry aerial part weights were the smallest in the case of 0.5 mM D-psicose, and the same applied to the fresh and dry underground part weights.

Further, on Dec. 18, 2003, a cherry tomato plant "petite" was transplanted for permanent planting to a hydroponic apparatus, and a total of 7 treated plots in which a plot without addition was added to 6 treated plots with the use of a nutrient solution supplemented with 0.05 mM or 0.5 mM D-psicose, D-fructose or mannitol were prepared. A survey was carried out with regard to the growth until 40 days after the permanent planting. As a result, the stem length was the shortest in the cases of 0.05 mM D-psicose and 0.05 mM D-fructose. Although a significant difference in the stem diameter was not observed among treated plots, however, a tendency was observed that the stem was slightly thinner in the treated plot of any of the sugars at a high concentration. A significant difference in the number of leaves was not observed among treated plots. A tendency was observed that the underground part weight was slightly smaller in the treated plot of any of the sugars compared with the control plot, and in particular, it was the smallest in the case of 0.5 mM D-psicose.

From the above result, it is presumed as follows.

The addition of D-psicose at a concentration of from 0.001% to 0.05 mM slightly promoted the growth of cherry tomato.

The addition of D-psicose at a concentration of 0.5 mM or more inhibited the growth of cherry tomato.

There was a possibility that a difference in the effect of a treatment by the addition of a sugar among varieties, growth stages or treatment periods is observed.

EXAMPLE 12

Effect of D-Allose on Growth of Cherry Tomato

[Purpose]

By using a nutrient solution supplemented with D-allose, a survey was carried out with regard to the growth of tomato during a stage of raising seedlings thereof.

[Materials and Methods]

On Jul. 13, 2004, seeds of a cherry tomato plant "mini carol" (Sakata Seed Co., Ltd.) were sown one by one in the respective holes using 30 holes among the 253 holes of a rockwool (280 mm (width)×580 mm (length)), which was placed in a plastic container with a capacity of 8 L. In this plastic container, 1 L of each nutrient solution in which a fertilizer (Otsuka No. 1 (1.5 g/L) and Otsuka No. 2 (1.0 g/L)) was dissolved was poured, then, the cultivation was carried out in a glass chamber without heating. With regard to a treated plot, 7 treated plots in which a treatment liquid obtained by adding D-allose at 0 to 5 mM to the fertilizer nutrient solution was poured in the plastic container from July 20 when the seeds germinated completely were prepared. Incidentally, the treatment liquid was added in the same amount to the respective treated plots according to need. A survey was carried out with regard to the growth at 4 weeks after the initiation of the treatment.
[Results]
The results of the survey of the growth at 4 weeks after the initiation of the treatment are shown in Table 6 (survey of the growth at 4 weeks after the initiation of the treatment)

The stem length was slightly longer in the treated plot of from 0.01 mM to 5.0 mM compared with the control plot, and in particular, the stem length increased most in the plot of 0.01 mM. The stem diameter increased most in the plot of 0.01 mM, and a significant difference was not observed among the other treated plots. The number of leaves was the smallest in the plot of 5.0 mM, however, a significant difference was not observed among the other treated plots. Both the fresh stem and leaf weights were the largest in the plot of 0.01 mM, while they were the smallest in the plot of 5.0 mM. In the plot of 0.01 mM and the plot of 0.05 mM, flowering was promoted compared with the other treated plots.

From the above result, in the case where D-allose was added to the fertilizer nutrient solution during raising seedlings of cherry tomato, effects of promoting the growth and promoting flowering were observed.

TABLE 6

| Test plot | Stem length (cm) | Stem diameter (mm) | Number of leaves | Number of opening flowers | Fresh stem weight (g) | Fresh leaf weight (g) |
|---|---|---|---|---|---|---|
| Plot of 0 mM (control plot) | 51.9 | 4.5 | 8.5 | 0.0 | 9.8 | 6.9 |
| Plot of 0.01 mM | 69.1 | 5.3 | 9.3 | 0.6 | 16.4 | 10.9 |
| Plot of 0.05 mM | 60.9 | 4.3 | 8.9 | 0.4 | 11.7 | 6.9 |
| Plot of 0.1 mM | 56.7 | 4.3 | 9.0 | 0.0 | 11.1 | 8.6 |
| Plot of 0.5 mM | 57.0 | 4.5 | 8.3 | 0.0 | 11.2 | 8.3 |
| Plot of 1.0 mM | 59.0 | 4.8 | 9.6 | 0.0 | 13.7 | 9.7 |
| Plot of 5.0 mM | 40.4 | 4.2 | 7.0 | z | 6.7 | 4.8 | z: Bud formation could not be confirmed.

In the case where D-allose was added to the fertilizer nutrient solution during raising seedlings of cherry tomato, an effect of promoting the growth and promoting flowering was observed.

EXAMPLE 13

Effect of Treatment with D-Psicose During Raising Seedlings of Rice

[Purpose]
Toward the practical application of a treatment with a rare sugar, an effect of the treatment during raising seedlings of rice was examined.
[Method of Treatment with D-Psicose]
A seedling of a rice plant (variety: Nihonbare, see FIG. 10, the middle of the photograph, the white bar: 5 mm) at day 5 after sowing was used for an experiment. The rice seedling was raised by hydroponic culture in a pot using Kimura B solution. The Kimura B solution was supplemented with D-psicose at each concentration. While the solution was replaced with the same solution every 5 days, cultivation was carried out for 10 days. Thereafter, the seedling was transplanted to a pot filled with soil, and then, cultivation was carried out with natural light in a glass chamber for 7 days. Then, total RNA was extracted and a Northern blot analysis was carried out.

[Results]
During raising the seedling, the treatment with a liquid fertilizer in which D-psicose was mixed at a concentration of from 0.005 mM to 0.5 mM was carried out for 10 days, and after the treatment, the seedling was transplanted to a pot, and at 1 week thereafter, the behavior of genes related to resistance was confirmed (FIG. 11). As a result, in the case where the seedling was raised with the liquid fertilizer supplemented with D-psicose at 0.5 mM, induction of PBZ1, which is a gene related to resistance (one of the PR genes whose expression is induced by probenazole) and chitinase gene (PCG3) was strongly observed (FIG. 11). In the treated plots of from 0.0005 to 0.1 mM, either of the genes was not expressed, however, no effect was observed on PAL gene which was expressed constantly under this condition.

By this treatment, inhibition of the growth of the plant body was observed [Table 6 (effect of treatment with D-psicose during raising seedlings of rice) and FIG. 12]. By the treatment with 0.5 mM D-psicose starting from day 5 after germination, the plant length and the root length were inhibited to 43% and 67%, respectively, relative to those of the untreated plot at day 5 (Table 7). However, there was no change in the number of roots (Table 7).

TABLE 7

| Number of days after germination | Treated with D-psicose | Plant length (cm) | Seed root length (cm) | Number of roots (roots) |
|---|---|---|---|---|
| Day 5 | non | 2.33 ± 0.12 | 4.81 ± 0.81 | 4.24 ± 0.36 |
| Day 10 | non | 12.08 ± 0.21 | 7.58 ± 0.23 | 7.00 ± 0.6 |
| Day 10 | 0.5 mM | 5.29 ± 0.58 | 5.15 ± 0.26 | 7.00 ± 0.6 |

Subsequently, it was examined whether this inhibition is a transient action during the treatment or inhibition irreversibly occurs once the plant received the treatment. As a result, the plant length recovered to 52.4% in 1 week after transplanting the plant to a pot after the treatment with D-psicose compared with the untreated plot, and it recovered to about 80% in 2 weeks after the transplantation [Table 8 (persistence of the effect of D-psicose on inhibiting the growth of rice) and FIG. 13].

TABLE 8

| Number of days after transplantation to pot | Plant length (cm) | |
|---|---|---|
| | Untreated | Treated with 0.5 mM D-psicose |
| 7 | 31.4 ± 0.5 | 16.5 ± 2.4 (52.4%) |
| 14 | 44.7 ± 0.1 | 35.3 ± 2.1 (78.8%) |

The values in the parenthesis represent the percentages of the relative values to those of untreated plots.

[Discussion]

Various effects of D-psicose, which is one of the rare sugars, have been made clear. Among these, it was also made clear that D-psicose exhibits an activity of inducing expression of genes related to resistance in a plant and has an elicitor function. Accordingly, by performing a treatment with D-psicose only in a limited period in a closed system, i.e., during raising seedlings of rice, expression of genes related to resistance and what effect is given to rice were examined.

As a result, it induced the expression of genes related to resistance as expected, and this induction was persisted after the plant was transplanted to the pot after completion of the treatment with D-psicose and the effect was persisted for at least from 1 week (FIG. 11) to 10 days. Further, by this treatment, inhibition of the growth during the hydroponic culture was observed, however, in about 2 weeks after being transplanted to the pot, the plant was grown without making much difference with that in the untreated plot. Therefore, it was made clear that the action of inhibiting the growth of D-psicose is not an irreversible action.

In general, overgrown roots in a nursery bed are mechanically cut when rice seedlings were transplanted to a paddy field after raising seedlings. Considering this fact, it was presumed that inhibition of the growth of roots during raising seedlings is useful as long as it does not affect the growth thereafter. Further, if transient growth inhibition at the time of treatment and improvement of disease resistance can be expected, by performing a treatment in a similar manner to an agent to be applied by throwing before falling down of rice is predicted, it may be possible to inhibit the growth transiently. In general, there are many cases in which a dwarfing character links to disease resistance, and it may be possible to consider that the results of this study are in the same case.

In the case where D-psicose was added to the fertilizer nutrient liquid during raising seedlings of rice, an effect of growth inhibition was observed. However, this action was a transient action, and when D-psicose was eliminated, the growth recovered. It is considered that this phenomenon is useful for raising healthy (robust) rice seedlings or preventing falling down of rice.

EXAMPLE 14

Effect of D-Psicose on Promoting Growth in Tissue Culture of *Phalaenopsis orchid* and *Cymbidium*

[Material and Methods]

Flask seedlings of *Phalaenopsis orchid* and *Cymbidium* obtained by tissue culture were used in an experiment.

As for *Phalaenopsis orchid*, MS medium supplemented with D-psicose, D-glucose or D-fructose at a concentration of 0.005% (w/v) was used, and the flask seedlings were aseptically transplanted on Sep. 6, 2004. As for the number of seedlings, 4 seedlings were used for 1 test plot, and glass bottles with a capacity of 500 ml and having a hole with a diameter of about 1 cm for preventing dew condensation made in the upper region was used as culture containers. The cultivation was carried out in a culture chamber at 25° C. and 5,000 Lux (12-hour day length) Then, on Jan. 24, 2005, a survey was carried out with regard to the growth conditions of aerial part and underground part and the number of roots. The results are shown in Table 8 (effect of addition of D-psicose on the growth of seedlings of *Phalaenopsis orchid*).

As for *Cymbidium*, in the same manner as the above *Phalaenopsis orchid*, MS medium supplemented with D-psicose, D-glucose, D-fructose or D-allose was used, and the flask seedlings were aseptically transplanted on Oct. 4, 2004. At this time, 4 or 5 leaves and 2 roots were left and the rest of them were cut off using a knife. As for the number of seedlings, 4 seedlings were used for 1 test plot, and glass bottles with a capacity of 900 ml and having a hole with a diameter of about 1 cm for preventing dew condensation made in the upper region was used as culture containers. The cultivation was carried out in a culture chamber at 25° C. and 5,000 Lux (12-hour day length) Then, on Feb. 1, 2005, a survey was carried out with regard to the growth conditions of aerial part and underground part, the number of roots and the number of lateral buds. The results are shown in Table 9 (effect of addition of rare sugar on the growth of seedlings of *Cymbidium*).

[Results and Discussion]

D-psicose was added to the tissue culture medium for Phalaenopsis orchid at a concentration of 0.005% (w/v), and an effect thereof on the growth was examined. As a result, a tendency was observed that the aerial part weight, the underground part weight, and the number of roots were all increased by adding D-psicose compared with the plot without addition, which was a control plot, the plot of D-glucose addition and the plot of D-fructose addition. From this result, it was made clear that D-psicose exhibits an effect on promoting the growth of *Phalaenopsis orchid*.

Further, D-psicose or D-allose was added to the tissue culture medium for *Cymbidium* at a concentration of 0.005% (w/v), and an effect thereof on the growth and the like was examined. As a result, a tendency was observed that the aerial part weight, the number of roots and the number of lateral buds were increased by adding D-allose compared with the plot without addition, which was a control plot, the plot of D-glucose addition and the plot of D-fructose addition. The addition of D-psicose resulted in an increase in the number of lateral buds to a certain degree, however, the observed effect was not as much as that of the case of *Phalaenopsis orchid*.

From this result, it was made clear that D-psicose and D-allose exhibit an effect on promoting the growth or an effect on promoting the formation of lateral buds for seedlings of orchids introduced to Japan from the West such as *Phalaenopsis orchid* and *Cymbidium*. It was made clear that by selecting a rare sugar to be added according to the type of a target plant or the purpose, promotion of growth or formation of lateral buds can be achieved.

TABLE 9

| Addition to medium | Aerial part weight (g) | Underground part weight (g) | Number of roots (roots) |
| --- | --- | --- | --- |
| non | 4.7 | 2.9 | 12.5 |
| 0.005% D-glucose | 5.1 | 3.7 | 12.3 |
| 0.005% D-frucose | 5.7 | 4.0 | 14.8 |
| 0.005% D-psicose | 6.1 | 4.1 | 16.0 |

(Note)
The numerical values represent the averages of the four plants.

TABLE 10

| Addition to medium | Aerial part weight (g) | Underground part weight (g) | Number of roots (roots) | Number of lateral buds (buds) |
| --- | --- | --- | --- | --- |
| non | 2.1 | 3.8 | 10.8 | 0 |
| 0.005% D-glucose | 1.9 | 2.9 | 9.5 | 0 |
| 0.005% D-frucose | 2.0 | 3.8 | 10.0 | 0 |
| 0.005% D-psicose | 2.0 | 4.1 | 10.8 | 0.5 |
| 0.005% D-allose | 2.7 | 4.0 | 12.8 | 3.8 |

(Note)
The numerical values represent the averages of the four plants.

EXAMPLE 15

Effect of D-Psocose on *Fusarium wilt* of Tomato

[Materials and Methods]

By using a tomato plant and a strain of *Fusarium oxysporum*, which is a typical pathogenic bacterium of tomato, an effect of D-psicose during infection in a stage of raising seedlings thereof was examined.

To be more specific, seeds of a tomato plant (variety: "House Momotaro") were subjected to an immersion treatment by immersing them in a 0.01% (w/v) D-psicose solution or a 0.007% (w/v) probenazole solution for 15 minutes while stirring slowly, followed by air-drying on sterile gauze, and then used as treated seeds. In the medium culture for raising seedlings (pete:pearlite:vermiculite=2:1:1), 0.01% (w/v) D-psicose or 0.007% (w/v) probenazole was mixed, and the soil was placed in black polypot plant containers with a diameter of 9 cm, and then, 4 seeds of the above treated seeds were sown in each pot. The seeds (20 seeds in total) were sown in 5 pots for each test plot. After sowing, the pots were placed in a growth chamber at 23° C. and 5,000 Lux (12-hour day length), and raising of seedlings was initiated. At 1 month and 2 months after the initiation of raising of seedlings, a suspension of mycelium of *Fusarium oxysporum* (IFO 31213 strain) was inoculated around the roots, whereby infection with *Fusarium oxysporum* was caused. After the inoculation of *Fusarium oxysporum*, the temperature was raised to 30° C., and cultivation was continued. At about 4 months after sowing, a survey was carried out with regard to the survival rate of plants, the conditions of browning of vascular bundles and roots, the stem diameter and the like.

[Results and Discussion]

As a result of examining an effect of a rare sugar on *Fusarium wilt*, which is a typical disease of tomato, even by subjecting seeds to an immersion treatment with a D-psicose solution, an inhibitory effect on *Fusarium wilt* thereafter was observed, and the effect is equal to or more than that of probenazole (FIG. 14). To be more specific, while the vascular bundle browning ratio in the case where the treatment of seeds was not carried out was 25%, the vascular bundle browning ratio in the case where the treatment was carried out with D-psicose or probenazole was decreased to 5%. In addition, the stem diameter was increased along with it. Even in the observation of external appearance, in the case where the treatment of seeds with D-psicose was carried out, the plants were close to healthy plants compared with the case that the treatment of seeds was not carried out, and the healthiness thereof was higher than that of the case of treatment with probenazole. Further, in the case where addition of the compound to the medium culture was also carried out, although yellow discoloration of leaves which is considered to be chemical damage was slightly caused, the degree of the chemical damage caused by D-psicose was smaller than that of the case of probenazole, and the degree of decrease in the stem diameter was small.

From the above result, it was made clear that the treatment of seeds with D-psicose or the addition of D-psicose to the medium culture has an effect on inhibiting tomato *Fusarium oxysporum*.

EXAMPLE 16

[Material and Methods]

In the process of cultivation of eggplant, an effect of spraying D-psicose was examined.

An eggplant plant (variety: "Senryo NiGo") was used in an experiment. Eggplant seedlings were transplanted for permanent planting to No. 7 unglazed pots filled with "Hana to Yasai no Tsuchi (garden soil for flowers and vegetables)" and a cultivation test was carried out in a vinyl house equipped with a heating device. As a fertilizer, 4 granules of IB compound fertilizer per pot were given around the roots, and irrigation was carried out by automatically feeding 500 ml of water twice a day. During the cultivation, on a weekly basis, water, a 0.2% (w/v) D-glucose solution or a 0.2 (w/v) D-psicose solution was sprayed onto the whole plant. As for the number of eggplant plants, 10 plants were used for each group, and the cultivation was carried out twice, i.e., in summer (from May 14 to Jul. 15, 2004) and in winter (from Nov. 4, 2004 to Feb. 24, 2005). A survey was carried out with regard to the growth conditions during the cultivation and yield of fruits.

[Results and Discussion]

In the eggplant cultivation, although a significant effect of spraying the D-psicose solution was not observed in summer, promotion of the growth (an increase in the aerial part weight and the underground part weight) and an increase in the yield of fruits were observed in winter (FIG. 15). Eggplant is a summer vegetable, and prefers to a relatively high temperature during the cultivation. However, in the test performed in winter, the lowest temperature at night decreased to around 5° C. although the heating device was provided, therefore, it is presumed that it became a considerably large stress for eggplant. In such a circumstance, the event that promotion of the growth and an increase in the yield by spraying the D-psicose solution were observed is considered to be an effect of D-psicose on improving resistance to a low temperature stress in winter in eggplant.

EXAMPLE 17

[Material and Methods]

In the process of cultivation of tomato, an effect of spraying D-psicose was examined.

A tomato plant (variety: "Momotaro") was used in an experiment. Tomato seedlings were transplanted for permanent planting to No. 7 unglazed pots filled with "Hana to Yasai no Tsuchi (garden soil for flowers and vegetables)" and a cultivation test was carried out in a vinyl house equipped with a heating device. As a fertilizer, 4 granules of IB compound fertilizer per pot were given around the roots, and irrigation was carried out by automatically feeding 500 ml of water twice a day. During the cultivation, on a weekly basis, water, a 0.2% (w/v) D-glucose solution or a 0.2% (w/v) D-psicose solution was sprayed onto the whole plant. As for the number of tomato plants, 10 plants were used for each group, and the cultivation was carried out twice, i.e., in summer (from April 20 to Aug. 9, 2004) and in winter (from Nov. 4, 2004 to Mar. 14, 2005). A survey was carried out with regard to the growth conditions during the cultivation and yield of fruits.

[Results and Discussion]

In the tomato cultivation, although a significant effect of spraying the D-psicose solution was not observed in summer, an increase in the number of fruits and the yield of fruits were observed in winter (FIG. 16). Tomato is a summer vegetable, and prefers to a relatively high temperature during the cultivation. However, in the test performed in winter, the lowest temperature at night decreased to around 5° C. although the heating device was provided, therefore, it is presumed that it became a considerable large stress for tomato. In such a circumstance, the event that promotion of the growth and an increase in the yield by spraying the D-psicose solution were observed is considered to be an effect of D-psicose on improving resistance to a low temperature stress in winter in tomato.

EXAMPLE 18

[Materials and Methods]

It is known that an oligosaccharide such as a chitin oligosaccharide or a derivative of sucrose which is a disaccharide (such as palatinose or fluorosucrose) acts on a plant as an elicitor (a substance that induces biological defense) and induces various defense responses. From these facts, it has been expected that also a rare sugar such as D-psicose may exhibit an elicitor action in a plant and cause improvement of disease resistance or the like.

Therefore, by using a tomato plant and a strain of *Fusarium oxysporum*, which is a typical pathogenic bacterium of tomato, an effect of D-psicose during infection was examined.

To be more specific, seeds of a tomato plant (variety: "House Momotaro") were subjected to an immersion treatment by immersing them in a D-psicose solution at a concentration of from 0.01% (w/v) to 0.1% (w/v) for 15 minutes while stirring slowly, followed by air-drying on sterile gauze, and then used as treated seeds. At the center of a plastic dish with a diameter of 9 cm filled with 25 ml of 1% (w/v) agar, a mycelial disc (diameter: 1 cm) obtained by pushing out *Fusarium oxysporum* (IFO 9967 strain and IFO 31213 strain) cultured for 1 week on a potato dextrose agar medium using a cork borer along with the agar medium was placed, and 10 seeds of the above treated seeds were placed equally spaced around the disc. At this time, test plots in which D-psicose was added to the agar medium at a concentration of from 0.01% (w/v) to 0.1% (w/v) were prepared. Then, the dishes were placed at 23° C. under the dark condition for 7 days to 10 days, and observation was carried out with regard to the elongation of shoot, the elongation of root, the shoot development rate, the infection state in root and the like. The results are shown in Table 11.

TABLE 11

| *Fusarium oxysporum* | Treated with D-psicose | | Shoot length (cm) | Root length (cm) |
| --- | --- | --- | --- | --- |
| | Seed | Medium | | |
| non | non | non | 5.7 | 7.5 |
| non | 0.05% | non | 6.7 | 7.4 |
| IFO 9967 strain | non | non | 5.6 | 3.7 |
| | 0.01% | non | 5.1 | 4.1 |
| | 0.05% | non | 3.4 | 3.3 |
| | 0.10% | non | 4.3 | 3.7 |
| | 0.01% | 0.01% | 5.2 | 4.5 |
| | 0.05% | 0.05% | 5.7 | 3.7 |
| | 0.10% | 0.10% | 3.8 | 2.0 |
| IFO 31213 strain | non | non | 3.2 | 2.8 |
| | 0.01% | non | 4.7 | 3.9 |
| | 0.05% | non | 4.2 | 3.8 |
| | 0.10% | non | 3.0 | 3.2 |
| | 0.01% | 0.01% | 4.5 | 4.7 |
| | 0.05% | 0.05% | 4.5 | 3.5 |
| | 0.10% | 0.10% | 2.9 | 2.1 |

(Note)
The numerical values represent the averages of the ten seeds.

[Results and Discussion]

As a result of the experiment of infection of tomato with *Fusarium oxysporum*, in the case where IFO 31213 strain was used as the *Fusarium oxysporum*, by the immersion treatment with the 0.01% (w/v) and 0.05% (w/v) D-psicose solutions, the failure of elongation of shoots or roots caused by the infection at the time of germination was alleviated. However, when the concentration of D-psicose in the solution was 0.1% (w/v) the shoot length and the root length were both decreased. It was considered that this was caused by a direct effect of D-psicose on inhibiting elongation.

In addition, by adding D-psicose to the agar medium in the infection experiment, mycelial elongation of *Fusarium oxysporum* was inhibited and the failure of elongation of shoots or roots were further alleviated.

In both the plot in which the seeds were treated with D-psicose and the plot in which further D-psicose was added to the agar medium, improvement of the shoot development rate and reduction of browning caused by infection of roots with *Fusarium oxysporum* were observed. On the other hand, in the case where IFO 9967 strain was used as the *Fusarium oxysporum*, the observed effect on improving the failure of elongation of shoots or roots was not as significant as that of the case of using IFO 31213 strain. It is considered that this is because the infectivity or the ability to cause a disease of IFO 9967 strain was weaker than that of IFO 31213 strain. However, improvement of shoot development rate and reduction of browning caused by infection of roots with *Fusarium oxysporum* could be observed in the same manner as the case of using IFO 31213 strain.

From the above result, it was confirmed that by treating tomato seeds with D-psicose, the failure caused by infection with *Fusarium oxysporum* can be reduced, and further by adding D-psicose to the medium, mycelial elongation of *Fusarium oxysporum* was inhibited and the effect is increased. From this, it was made clear that D-psicose is useful for improving plant disease resistance.

EXAMPLE 19

[Materials and Methods]

By using as targets, *Fusarium oxysporum, Glomerella cingulata, Verticillium dahliae* and *Botrytis cinerea*, which are typical plant pathogenic bacteria, an effect of a rare sugar on mycelial elongation was examined.

As the test bacterial strains, IFO 31213 strain, IFO 6425 strain, IFO 9765 strain and IFO 9760 strain were used.

Each test bacterial strain was cultured on a potato dextrose agar medium at 23° C. for 7 days, and the cultured bacterium was pushed out along with the agar medium in such a manner that the agar medium had a diameter of 1.1 cm, which was placed at the center of a dish filled with an agar medium supplemented with a rare sugar at 0.05% (w/v) and cultured at 23° C. for 7 days. After the cultivation, the length of the extending mycelium was measured.

The results are shown in Table 12.

TABLE 12

| Fusarium oxysporum | Treated with D-psicose | | Survival rate (%) | Vascular bundle browning ratio (%) | Leaf browning ratio (%) | Plant length (cm) | Aerial part weight (g) |
| --- | --- | --- | --- | --- | --- | --- | --- |
| | Seed | Medium | | | | | |
| Without addition | non | non | 100 | 0 | 0 | 31.4 | 2.6 |
| | 0.10% | non | 100 | 0 | 0 | 17.8 | 2.2 |
| Added | non | non | 28 | 79 | 100 | 14.0 | 1.9 |
| | 0.01% | non | 28 | 39 | 100 | 14.5 | 1.9 |
| | 0.10% | non | 16 | 60 | 100 | 13.9 | 2.2 |
| | 0.01% | 0.01% | 50 | 45 | 5 | 17.6 | 3.1 |
| | 0.10% | 0.10% | 25 | 38 | 13 | 13.8 | 3.3 |

(Note)
The numerical values represent the averages of the 20 plants.

[Results and Discussion]

As a result of measuring the mycelial elongation of the respective plant pathogenic bacteria, D-altrose exhibited the highest inhibitory effect on any of the pathogenic bacteria, followed by D-allose and D-psicose. From the above result, it was made clear that a rare sugar such as D-altrose, D-allose or D-psicose has an effect on inhibiting mycelial elongation of a plant pathogenic bacterium.

EXAMPLE 20

[Materials and Methods]

With regard to *Pythium ultimum* that causes damping-off of spinach and the like, an effect of a rare sugar on oospore formation was examined.

*Pythium* fungi belong to the zoosporic genera and perform sexual reproduction by archegonia and antheridia and form oospores. The oospore germinates when an appropriate condition of temperature and humidity is provided, and forms a mycelium or a zoospore and rapidly spreads by infecting plants.

First, as the *Pythium ultimum*, IFO 32426 strain was used, and static culture thereof was carried out with 200 ml of V8 medium at 23° C. for 1 week. The resulting mycelial mat was well washed with sterile water and divided into 16 equal parts with forceps. This mycerial body was disentangled uniformly to form a small piece and immersed in 20 ml of a sugar solution at a concentration of 0.05% (w/v) and let stand at 23° C. for 4 days. Then, formation of an oospore was observed with a microscope. Further, the same experiment was carried out using *Pythium zingiberum* IFO 30817 strain.

[Results and Discussion]

The results of examining an effect of a rare sugar on the oospore formation of *Pythium ultimum* are shown in FIG. 17. In the photographs of FIG. 17, an observation of a state of the oospore formation with a microscope is shown, and a substance that looked like a black small particle is an oospore and a substance that looked like a thread is a mycelium of *Pythium ultimum*. It shows a state in which an oospore was formed by leaving the mycelium for 4 days from the state in which only the mycelium was present at the beginning.

When taking a look at FIG. 17, while there was no effect even when D-glucose or D-fructose was added (there was no difference with the control plot: plot without addition), by adding D-allose, oospore formation was not observed at all. Although the effect was smaller than that of D-allose, by adding L-galactose or D-psicose, oospore formation was also inhibited. A tendency of the degree of inhibition was as follows. D-allose>L-galactose>D-psicose. Further, a similar effect was also observed in the experiment using *Pythium zingiberum*.

From the above result, it was made clear that a rare sugar such as D-allose inhibits oospore formation against *Pythium pathogenic* fungi such as *Pythium ultimum* that causes catastrophic damage to agricultural crops and has an effect on preventing or inhibiting infection.

EXAMPLE 21

[Materials and Methods]

In the process of cultivation of strawberry, an effect of spraying D-psicose was examined.

A strawberry plant (variety: "*Sachinoka*") was used in an experiment. Strawberry seedlings were transplanted for permanent planting to a mixed culture medium of rockwool and peat moss, and then, by using Otsuka A prescription hydroponic nutrient solution, soilless culture was carried out in a glass house. During the cultivation, on a weekly basis, water, a 0.2% (w/v) D-glucose solution or a 0.2% (w/v) D-psicose solution was sprayed onto the whole plant. As for the number of strawberry plants, 17, 19 and 18 plants were used for the groups, respectively, and permanent planting was carried out on Sep. 24, 2004, and spraying was started from Oct. 22, 2004. A survey was carried out with regard to the growth conditions, the yield of fruits, the quality of fruits and the like by Mar. 7, 2005.

[Results and Discussion]

As a result of the survey with regard to the growth of strawberry, the yield of fruits, the quality of fruits and the like during cultivation, there was no significant difference in the growth and the total yield. However, in the plot of spraying D-psicose, promotion of flower-bud formation and acceleration of harvesting time accompanying it and improvement of the acidity and the content of vitamin C in the fruit were observed. It is known that the flower-bud formation of plants (FIG. 18) or the content of vitamin C in fruits (FIG. 19) is increased or promoted by any of a variety of stresses, it was presumed that the strawberry recognizes the spraying of D-psicose as a stress.

EXAMPLE 22

[Materials and Methods]

By using Primula, an effect of spraying D-psicose on a drying stress was examined. By using commercially available Primula planted in a pot, foliar spraying of water, a 0.2% (w/v) D-glucose solution or a 0.2% (w/v) D-psicose solution was carried out on the whole plant. After irrigation was sufficiently carried out from the lower part of the pot, the plant was left in a condition that no irrigation was carried out, and a wilted condition thereof was observed.
[Results and Discussion]

In the test plot in which foliar spraying of water or D-glucose was carried out, at one day after the initiation of the test, a wilt was observed in the whole plant, however, in the case where foliar spraying of D-psicose was carried out, the degree of wilt was slightly, and it took 2 days until an equivalent wilt occurred. From this result, it was made clear that spraying of psicose improves resistance to a drying stress.

EXAMPLE 23

Effect of Rare Sugar on Inhibiting Microorganism
[Materials and Methods]

By using as targets, *Aspergillus niger*, *Cladosporium cladosporioides* and *Penicillium chrysogenum*, which are typical filamentous fungi and generally seen in a living environment, an effect of a rare sugar on mycelial elongation was examined.

As the test fungal strains, NBRC 4066 strain, NBRC 4459 strain and NBRC 4626 strain were used.

Each test fungal strain was cultured on a potato dextrose agar medium at 25° C. for 7 days, and one in which the mycelium extended over the surface of the dish was pushed out along with the agar medium in such a manner that the agar medium was in a disc form with a diameter of 1.1 cm, which was placed at the center of a dish filled with an agar medium (1% Bacto agar) supplemented with any of a variety of rare sugars (allitol, D-altrose, L-mannose, L-galactose, D-tagatose, D-sorbose, D-psicose, D-allose, D-glucose and D-fructose) at 0.05% (w/v) and cultured at 25° C. for 4 days. After the cultivation, the length of the mycelium extending on the surface of the culture medium was measured. Two culture media were prepared for each test plot, and the mycelial length represents the average thereof.
[Results and Discussion]

The results are shown in Table 18. As a result of measuring the mycelial elongation of the respective filamentous fungi, although the effect varied depending on the type of filamentous fungus, it was confirmed that D-altrose, D-allose, D-psicose and L-galactose have an effect of inhibiting mycelial elongation. From this result, it was made clear that a rare sugar can be used as an antifungal agent.

INDUSTRIAL APPLICABILITY

There is a possibility that a rare sugar remarkably reduce the amount of agricultural chemical to be used, and it can be expected to become an innovative agricultural chemical that has almost no problems related to safety such as agricultural chemical residues and contamination in the environment. Further, not only is the present invention useful in plant cultivation, for example, inhibition of plant disease, but also it includes a method of inhibiting the growth of various harmful microorganisms, therefore, it is possible to use it also in fields such as food production processing, medical facilities, living environments and air-conditioning equipment.

Further, the present invention shows the possibility that a rare sugar, which is a monosaccharide composed of only carbon, oxygen and hydrogen without containing a harmful element such as chlorine by an organic synthesis such as a conventional agricultural chemical, can be used for regulating the growth of a plant in various scenes. From this fact, it was confirmed that a rare sugar can be used as various plant regulators which are safe and are not harmful to the natural world. In the future, by elucidating the detailed mechanism thereof, or examining an effect thereof on other plants and other growth stages in detail, it is expected that development of a plant growth regulator comprising a new rare sugar as a material will be accelerated. In the future, by making actions of different rare sugars further clearer and using them in various combinations, it may become possible to regulate the growth of a crop simply. It is expected that if it becomes possible to supply a crop in a period when the crop costs high in the market by shifting the time of harvesting by regulating the growth, an economic effect thereof will be higher.

BRIEF DESCRIPTION OF THE DRAWINGS

FIG. 1 is a diagram for illustrating induction of systemic acquired resistance by D-psicose.

FIG. 2 is a photograph substituted for a drawing showing a Northern blot analysis of expression of lipoxygenase gene in cut leaves of rough lemon.

FIG. 3 is a photograph substituted for a drawing showing a Northern blot analysis of expression of chitinase gene in cut leaves of rough lemon.

FIG. 4 is a view showing an effect of a sugar on strawberry fruit.

FIG. 5 is a view showing an effect of treatment with a rare sugar on the bud flush rate of cuttings of *Vitis kiusiana* Momiyama (the bars represent standard deviations).

FIG. 6 is a view showing an effect of psicose on breaking of dormancy for buds on dormant branches of grape "*Vitis vinifera* L." (the bars represent standard deviations).

FIG. 7 is a photograph substituted for a drawing showing an effect of D-psicose on germination of seeds of *Diospyros kaki*.

FIG. 8 is a view showing an effect of treatment with a rare sugar on germination of *Salsora komarovii*.

FIG. 9 is a view showing an effect of each of 8 types of ketoses on germination of *Arabidopsis thaliana* LER series.

FIG. 10 is a photograph substituted for a drawing showing a rice plant (variety: Nihonbare) at day 5 after sowing.

FIG. 11 is a photograph substituted for a drawing showing induction of expression of genes related to resistance by a treatment with D-psicose.

FIG. 12 is a photograph substituted for a drawing showing an effect of a treatment with D-psicose during raising seedlings of rice.

FIG. 13 is a photograph substituted for a drawing showing rice at day 14 after it was transplanted to the pot after completion of the treatment with D-psicose.

FIG. 14 is a view showing an effect of D-psicose on *Fusarium wilt* of tomato.

FIG. 15 is a view showing an effect of spraying a D-psicose solution on the growth and yield of eggplant in winter.

FIG. 16 is a view showing an effect of spraying a D-psicose solution on the yield of tomato fruit in winter.

FIG. 17 is a photograph showing an effect of a rare sugar on the oospore formation of *Pythium ultimum*.

FIG. 18 is a view showing an effect of spraying a D-psicose solution on the flower-bud formation of strawberry.

FIG. 19 is a view showing an effect of spraying a D-psicose solution on the quality of strawberry fruit.

FIG. 20 shows an effect on the mycelial elongation of a filamentous fungus.

FIG. 21 is a diagram for illustrating the mechanism of induction of systemic acquired resistance in a plant.

FIG. 22 is a linkage diagram of Izumoring.

FIG. 23 is a diagram for illustrating Izumoring of C6 at the lower portion of FIG. 22.

The invention claimed is:

1. A method of inducing systemic acquired resistance of a plant, the method comprising:
   supplying to the plant a rare sugar selected from the group consisting of D-psicose, a mixture of D-psicose and D-fructose, D-allose, D-altrose and L-galactose.

2. The method according to claim 1, wherein the induction of systemic acquired resistance comprises induction of an agricultural chemical action.

3. The method according to claim 1, wherein the induction of systemic acquired resistance comprises induction of inhibition of a plant disease.

4. The method according to claim 1, wherein the induction of systemic acquired resistance comprises induction of a plant growth regulatory factor.

5. The method according to claim 4, wherein the plant growth regulatory factor is a factor having an action selected from the group consisting of disease resistance, insect resistance, fruit maturation, breaking of dormancy, regulation of germination, drying resistance, resistance to environmental stresses, low temperature resistance, high temperature resistance, salt resistance, heavy metal resistance and promotion of flowering.

6. A method of regulating growth of a plant by promoting or inhibiting the growth of the plant, comprising:
   supplying to the plant a rare sugar selected from the group consisting of D-psicose, a mixture of D-psicose and D-fructose, D-allose and L-galactose.

7. A method of inhibiting growth of a filamentous fungus which is pathogenic in a plant, comprising:
   supplying to the plant a rare sugar selected from the group consisting of D-psicose, D-allose, D-altrose and L-galactose.

8. The method according claim 1, wherein the rare sugar is D-psicose.

9. The method according claim 1, wherein the rare sugar is a mixture of D-psicose and D-fructose.

10. The method according claim 1, wherein the rare sugar is D-altrose.

11. The method according to claim 1, wherein the rare sugar is L-galactose.

* * * * *